United States Patent [19]

Alt et al.

[11] Patent Number: 4,755,218
[45] Date of Patent: Jul. 5, 1988

[54] HALOACYL 1-SUBSTITUTED-1,2,3,4-TETRAHYDRO-ISOQUINOLINES AS HERBICIDE ANTIDOTES

[75] Inventors: Gerhard H. Alt, University City; Harrison R. Hakes, Ballwin; Ronald J. Brinker, St. Louis County, all of Mo.

[73] Assignee: Monsanto Company, St. Louis, Mo.

[21] Appl. No.: 815,101

[22] Filed: Dec. 31, 1985

[51] Int. Cl.⁴ ............................................ A01N 43/40
[52] U.S. Cl. ............................................ 71/94; 71/92; 71/93; 71/100; 71/118; 546/146
[58] Field of Search ................ 71/94, 118, 93, 100; 546/146

[56] References Cited

U.S. PATENT DOCUMENTS

| | | | |
|---|---|---|---|
| 2,813,872 | 11/1957 | Schmutz | 546/146 |
| 3,133,810 | 5/1964 | Hamm | 71/100 |
| 4,001,244 | 1/1977 | Yonan | 546/146 |
| 4,033,756 | 7/1977 | Hoffmann | 71/118 |
| 4,137,070 | 1/1979 | Pallos et al. | 71/100 |
| 4,334,073 | 6/1982 | Diehr | 546/146 |

FOREIGN PATENT DOCUMENTS

| | | | |
|---|---|---|---|
| 1114824 | 12/1981 | Canada | 71/94 |
| 2930450 | 2/1981 | Fed. Rep. of Germany | 71/94 |
| 79-3213 | 6/1979 | South Africa | 71/94 |

OTHER PUBLICATIONS

Mollow et al., "A New Method for Synthesizing 2-Acyl-, etc.," Chem. Abstr. 88: 136432s (1978).
Mndzhoyan et al., "Isoquinoline Derivatives, etc.," Chem Abstr. 76: 127207x (1972).
Pirdzhanov et al., "Isoquinoline Derivatives, etc.," Chem Abstr. 80: 3360e (1974).
Palmer, "The Structure and Reactions of Heterocyclic Compounds," (Edward Arnold, Ltd., 1967).

Primary Examiner—Glennon H. Hollrah
Assistant Examiner—Amelia Owens
Attorney, Agent, or Firm—J. Timothy Keane; William I. Andress

[57] ABSTRACT

Haloacyl 1-substituted-1,2,3,4-tetrahydroisoquinoline compounds are antidotes for thiocarbamate, triazine-type and acetamide herbicides. These antidote compounds are especially effective in safening acetamide herbicides used to control grassy and broadleaf weeds in corn.

3 Claims, 2 Drawing Sheets

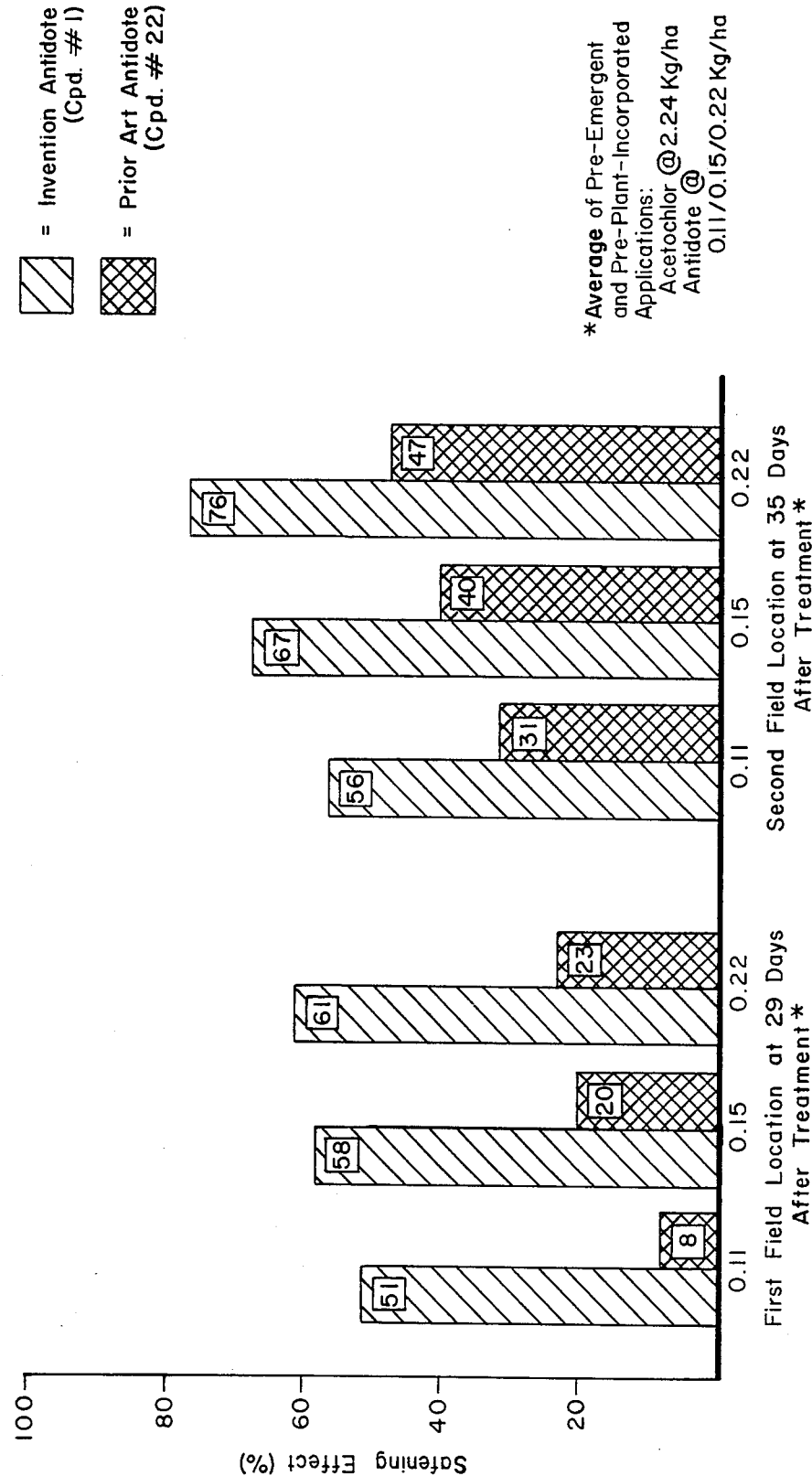

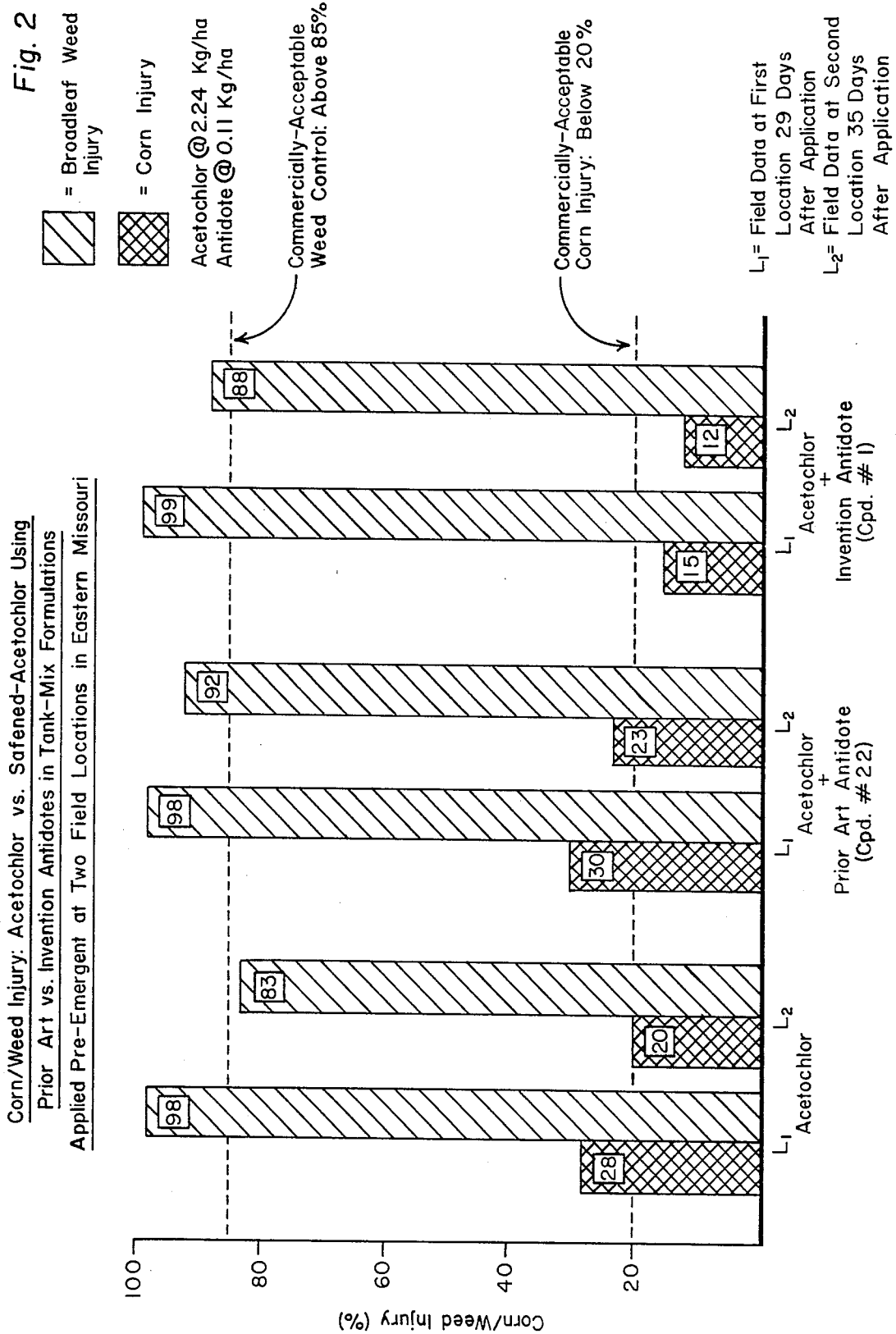

HALOACYL 1-SUBSTITUTED-1,2,3,4-TETRAHYDROISOQUINOLINES AS HERBICIDE ANTIDOTES

FIELD OF THE INVENTION

Herbicide antidotes are well-known crop protection chemicals. Of particular interest herein is a class of haloacyl 1-substituted-1,2,3,4-tetrahydroisoquinoline compounds found effective as antidotes for protecting crop plants from herbicide injury.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antidotes" or "safeners".

There are several classes of quinoline-type compounds known as antidotes for herbicides. U.S. Pat. No. 4,033,756 to Hoffmann describes the compound N-dichloroacetyl-1,2,3,4-tetrahydroisoquinoline as an antidote for protecting the seed of corn, grain sorghum and rice, from injury by thiocarbamate herbicides, such as triallate, or acetamide herbicides such as alachlor. Bayer South African Patent Application No. 79-3213 describes this same compound, N-dichloroacetyl-1,2,3,4-tetrahydroisoquinoline, as an antidote for protecting corn from a surface-applied pre-emergent treatment of a metazachlor-type herbicide. Bayer Canadian Pat. No. 1,114,824 describes the compound N-dichloroacetyl-1,2,3,4-tetrahydroquinaldine as an antidote for protecting corn from a surface-applied pre-emergent treatment of a metazachlor-type herbicide. Bayer West German Patent Application No. 29 30 450.5 describes the compound N-(α-chloropropionyl)-1,2,3,4-tetrahydroisoquinoline as an antidote for protecting corn from a surface-applied pre-emergent treatment of a metazachlor-type herbicide. U.S. Pat. No. 4,137,070 to Pallos et al describes a large class of acetamide antidote compounds including the compound dichloroacetyl-2-methyl-decahydroquinoline.

Weed control for corn crops is one of the oldest and most highly developed areas in weed science. Thus, for a herbicide product to be accepted commercially, such herbicide product must provide a relatively high level of control of both grassy and broadleaf weeds in corn, in addition to meeting several other criteria. For example, the herbicide must possess relatively high unit activity so that lower rates of herbicide application are feasible. Lower application rates are desirable in order to minimize exposure of the environment to the herbicide. At the same time, such herbicide must be selective in herbicidal effect so as not to injure corn crops. Herbicidal selectivity can be enhanced by use of an appropriate antidote in combination with the herbicide. But identification of an antidote having high safening activity suitable for a commercially-effective herbicide is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

DESCRIPTION OF THE INVENTION

Haloacyl 1-substituted-1,2,3,4-tetrahydro-isoquinoline compounds useful as antidotes against herbicide injury constitute a family of compounds having the general structural formula

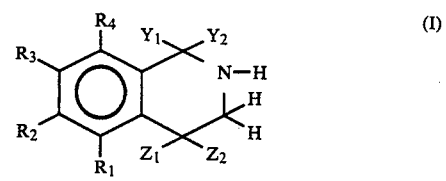

wherein X is haloacyl; wherein each of $Y_1$, $Y_2$, $Z_1$ and $Z_2$ is independently selected from hydrido, alkyl, aryl and haloalkyl, with the proviso that at least one of $Y_1$ and $Y_2$ must be a group other than hydrido; and wherein each of $R_1$, $R_2$, $R_3$ and $R_4$ is independently selected from hydrido, alkyl, alkoxy and haloalkyl.

The term "haloacyl 1-substituted-1,2,3,4-tetrahydroisoquinolines" is a general term to denote a class of compounds defined by formula I. All compounds of this class are characterized in having at least one substituent, other than hydrido, at the one-position of the heterocyclic ring. All compounds of this class are further characterized in that the isoquinoline heterocyclic three-position carbon has two hydrido groups attached to it. The term "haloacyl" is interchangeable with haloalkylcarbonyl" which embraces radicals derived from alkanoic acids, which radicals are substituted with one or more halogen atoms. Examples of haloacyl groups are monochloroacetyl, dichloroacetyl, dibromoacetyl, bromochloroacetyl, 2-chloro-1-oxopropyl, and 2,2-dichloro-1-oxopropyl. Where the term "alkyl" is used, either alone or within another term such as "haloalkyl" or "haloalkylcarbonyl", the term "alkyl" embraces linear or branched radicals having one to ten carbon atoms. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl and perfluoroethyl groups. The term "aryl" embraces phenyl and naphthyl groups. The term "alkoxy" embraces linear or branched oxy-containing alkyl radicals having one to ten carbon atoms, such as a methoxy group.

Also included in this invention are the stereo and optical isomers of compounds within the class defined by formula I.

Preferred compounds within formula I are haloacyl 1-substituted-1,2,3,4-tetrahydroisoquinolines wherein X is selected from haloacetyl and halo-propionyl groups. The term "haloacetyl" embraces methylcarbonyl radicals substituted with one or more halogen atoms, preferably selected from bromo and chloro groups. The term "halo-propionyl" embraces ethylcarbonyl radicals substituted with one or more halogen atoms, preferably the halo substitution being on the carbon adjacent the carbonyl moiety. Included within the terms "haloacetyl" and "halo-propionyl" are radicals having mixed halogen substitutions, that is, the alkyl moiety is substituted with at least one bromo atom and at least one chloro atom. Especially preferred antidote compounds are dichloroacetyl 1-substituted-1,2,3,4-tetrahydroisoquinolines.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used with benefit in combination with an antidote of the described class include thiocarbamates, triazines and acetamides. Such combinations can be used to obtain selective weed control with low crop injury in several varieties of monocotyledenous crop plants such as corn, grain sorghum (milo), and cereals such as wheat, rice, barley, oats and rye, as well as several varieties of dicotyledonous crop plants including oil-seed crops such as soybeans and cotton.

Examples of thiocarbamate herbicides are the following:
cis-/trans-2,3-dichloroallyl-diisopropylthiolcarbamate (common name "diallate");
ethyl dipropylthiocarbamate (common name "EPTC");
2,3,3-trichloroallyl-diisopropylthiolcarbamate (common name "triallate");
S-ethyl diisobutyl(thiocarbamate) (common name "butylate");
S-propyl dipropyl(thiocarbamate) (common name "vernolate")".

Examples of triazine herbicides are the following:
2-chloro-4,6-bis(ethylamino)-1,3,5-triazine (common name "simazine");
2-chloro-4-ethylamino-6-isopropylamino-sym-triazine (common name "atrazine");
2-chloro-4-(1-cyano)-1-methyl(ethylamino)-6-ethylamino-1,3,5-triazine (common name "cyanazine).

Examples of acetamide herbicides are the following:
2-chloro-N-isopropylacetanilide (common name "propachlor");
2-chloro-2'-(1,1-dimethylethyl)-6'-methyl-N-(methoxymethyl)acetanilide;
N-(butoxymethyl)-2-chloro-N-[2-(1,1-dimethylethyl)-6-methylphenyl]acetamide (common name "terbuchlor");
2-chloro-2',6'-diethyl-N-(methoxymethyl)acetanilide (common name "alachlor");
2-chloro-N-(isobutoxymethyl)-2',6'-acetoxylidide;
2-chloro-2',6'-diethyl-N-(butoxymethyl)acetanilide (common name "butachlor");
2-chloro-N-(ethoxymethyl)-6'-ethyl-o-acetotoluidide (common name "acetochlor");
2-chloro-N-(2,6-dimethyl-1-cyclohexen-1-yl)-N-(2-ethoxyethyl)acetamide;
ethyl ester of N-chloroacetyl-N-(2,6-diethylphenyl)glycine (common name "diethatyl ethyl");
2-chloro-N-(2,6-dimethylphenyl)-N-(2-methoxyethyl)acetamide (common name "dimethachlor");
2-chloro-N-(2-methoxy-1-methylethyl)-6'-ethyl-o-acetotoluidide (common name "metolachlor");
2-chloro-2',3'-dimethyl-N-(isopropyl)acetanilide;
2-chloro-2'-methyl-6'-methoxy-N-(propoxymethyl)acetanilide;
2-chloro-2'-methyl-6'-methoxy-N-(isopropoxymethyl)acetanilide;
2-chloro-2'-methyl-6'-ethoxy-N-(propoxymethyl)acetanilide;
N-(ethoxymethyl)-N-(2-ethyl-6-methyl-1-cyclohexen-1-yl)-2-chloroacetamide;
N-(ethoxymethyl)-N-(2,5-dimethyl-1-cyclopenten-1-yl)-2-chloroacetamide;
2-chloro-2',6'-dimethyl-N-(1-pyrazol-1-ylmethyl)acetanilide (common name "metazachlor");
2-chloro-N-(2,6-dimethyl-1-cyclohexen-1-yl)-N-(1H-pyrazol-1-ylmethyl)acetamide;
2-chloro-6'-trifluoromethyl-N-(isopropoxymethyl)acetanilide;
2-chloro-2'-methyl-6'-trifluoromethyl-N-(ethoxymethyl)acetanilide;
2-chloro-2'-trifluoromethyl-6-methyl-N-(propoxymethyl)acetanilide;
2-chloro-2'-methyl-6'-trifluoromethyl-N-(isopropoxymethyl)acetanilide;
2-chloro-2'-(3-methylbutoxy)-6'-methyl-N-(methyl)acetanilide;
2-chloro-2'-isobutoxy-6'-methyl-N-(propoxymethyl)acetanilide;
2-chloro-2'-methyl-6'-propoxy-N-(methyl)acetanilide;
2-chloro-2'-butoxy-6'-methyl-N-(methyl)acetanilide;
α-chloro-N-(ethoxymethyl)-N-[2-methyl-1-(1-methylethyl)-1-propenyl]acetamide;
2-chloro-2'-ethyl-6'-(2-methylpropoxy)-N-(ethoxymethyl)acetanilide;
2-chloro-2'-methyl-6'-(1-methylbutoxy)-N-(methyl)acetanilide;
2-chloro-2'-ethyl-6'-(1-methylpropyl)-N-(methyl)acetanilide;
2-chloro-2'-(1,3-dimethylbutoxy)-6'-methyl-N-(methyl)acetanilide;
2-chloro-2'-methyl-6'-(1-methylpropyl)-N-(methyl)acetanilide;
2-chloro-2'-ethyl-6'-trifluoromethyl-N-(1-pyrazolyl-1-ylmethyl)acetanilide;
2-chloro-N-isopropyl-1-(3,5,5-trimethylcyclohexen-1-yl)acetamide (common name "trimexachlor").

A preferred combination of herbicide and antidote which provides selective weed control and low crop injury is provided by an antidote compound of formula I and a herbicide compound selected from triallate, atrazine and an acetanilide compound of formula II:

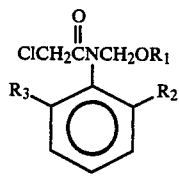

wherein $R_1$ is a linear or branched alkyl group of one to ten carbon atoms and wherein each of $R_2$ and $R_3$ is independently selected from hydrido, linear or branched alkyl groups of one to ten carbon atoms, alkoxy having a linear or branched alkyl portion of one to ten carbon atoms, alkoxyalkyl having linear or branched alkyl portions of one to ten carbon atoms, haloalkyl having a linear or branched alkyl portion of one to ten carbon atoms substituted with one or more halo groups selected from iodo, bromo, chloro and fluoro, with the proviso that when $R_2$ is ethyl and $R_3$ is ethyl, then $R_1$ cannot be methyl.

Preferred herbicide compounds of formula II are those wherein $R_1$ is a linear or branched alkyl group of one to five carbon atoms and wherein each of $R_2$ and $R_3$ is independently selected from linear or branched alkyl groups of one to five carbon atoms, alkoxy groups having linear or branched portions of one to five carbon atoms, and perfluoroalkyl groups having branched or linear alkyl portions of one to five carbon atoms.

Especially preferred herbicide compounds within formula II are those embraced by formula III:

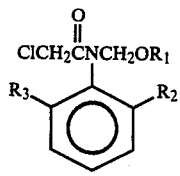

wherein $R_1$ is selected from methyl, ethyl, n-propyl, isopropyl, n-butyl, isobutyl, sec-butyl and tert-butyl; $R_2$ is selected from methyl, ethyl, methoxy, ethoxy, and trifluoromethyl groups; and $R_3$ is selected from methyl or ethyl. A particularly-preferred herbicide is the acetanilide compound of formula IV:

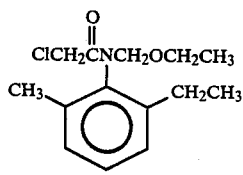

having the common name acetochlor and these alternative formal names:
2-chloro-N-(ethoxymethyl)-6'-ethyl-o-acetotoluidide or
2-chloro-2'-methyl-6'-ethyl-N-(ethoxymethyl)acetanilide or
2-chloro-N-ethoxymethyl-2'-methyl-6'-ethyl-acetanilide;

Another particularly-preferred herbicide is the acetanilide compound of formula V:

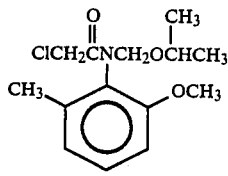

having the formal name 2-chloro-2'-methyl-6'-methoxy-N-(isopropoxymethyl)acetanilide;

Another particularly-preferred herbicide is the acetanilide compound of formula VI:

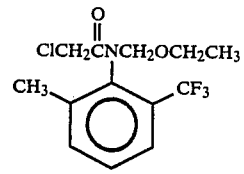

having the formal name 2-chloro-2'-methyl-6'-trifluoromethyl-N-(ethoxymethyl)acetanilide.

Several of the mentioned herbicides are known in the art. Diallate and triallate herbicides are described in U.S. Pat. No. 3,330,643 and No. 3,330,821. Atrazine herbicide is described in U.K. Pat. No. 814,947. Alachlor, butachlor and acetochlor herbicides are described in U.S. Pat. No. 3,442,945 and No. 3,547,620. Propachlor herbicide is described in U.S. Pat. No. 2,863,752 and Pat. No. Re. 26,961. Metolachlor herbicide is described in U.S. Pat. No. 3,937,730. Metazachlor herbicide is described in U.S. Pat. No. 4,249,935. Trimexachlor herbicide is described in U.S. Pat. No. 4,319,918. U.S. Pat. No. 4,351,667 describes the herbicides N-(ethoxymethyl)-N-(2-ethyl-6-methyl-1-cyclohexen-1-yl)-2-chloroacetamide and N-(ethoxymethyl)-N-2-(2,5-dimethyl-1-cyclopenten-1-yl)-2-chloroacetamide. U.K. Pat. No. 2,072,175 describes the herbicide 2-chloro-2'-methyl-6'-methoxy-N-(isopropoxymethyl)acetanilide. U.K. Pat. No. 2,072,181 describes the herbicide 2-chloro-2'-methyl-6'-trifluoromethyl-N-(ethoxymethyl)acetanilide.

Antidote compounds of the class defined by formula I reduce herbicidal injury to grain sorghum (milo), wheat, rice, soybean and corn, especially where herbicide injury is associated with pre-emergent application of the herbicides. Antidote compounds of the invention have been found particularly effective to reduce injury to corn caused by the acetamide herbicides acetochlor and 2-chloro-2'-methyl-6'-methoxy-N-(isopropoxymethyl)acetanilide, both of which are highly active acetanilide herbicides.

Acetochlor is especially suitable for use in corn for control of a greater variety of grassy and broadleaf weeds than typically provided by the commercial herbicide alachlor. Antidotes from the class defined by formula I, above, in combination with acetochlor have been found to have many advantages over alachlor for control of troublesome grassy and broadleaf weeds in corn. For example, these antidote+acetochlor combinations effectively control broadleaf weeds, such as velvetleaf, morningglory, and common purslane, as well as grassy weeds, while alachlor does not consistently control or suppress these broadleaf weeds. Surprisingly, antidotes within the formula I class, above, reduce injury to corn due to acetochlor, without interfering with the efficacy of acetochlor as a herbicide in corn. In addition to broader spectrum weed control, acetochlor provides several other advantages over alachlor, namely, higher unit activity, lower application rates in most soils and higher activity in high organic matter soils. For those weeds controlled effectively by both acetochlor and alachlor, acetochlor provides equivalent weed control at about one-half the application rate of alachlor. This lower effective application rate for acetochlor translates into substantially lower exposure of herbicide to the environment. By use of one of the above-described antidotes in combination with acetochlor, all of these advantages of acetochlor are available to improve corn production at a lower unit cost.

BRIEF DESCRIPTION OF THE DRAWINGS

FIG. 1 is a graph comparing the safening efficacy of invention and prior art antidotes on acetochlor herbicide treatments of corn at two different field locations.

FIG. 2 is a graph comparing corn-and-weed injury caused by treatment with acetochlor alone, by treatment with safened-acetochlor using a prior art antidote, and by treatment with safened-acetochlor using an invention antidote, at two different field locations.

ANTIDOTE COMPOUND PREPARATION

The haloacyl 1-substituted-1,2,3,4-tetrahydroisoquinoline antidote compounds of the invention may be prepared by the following general methods:

Step I(a):

An phenethylamine is reacted with an acyl halide to form an amide-containing compound which is cyclized in the presence of phosphorus pentoxide to form a dihydroisoquinoline intermediate.

Step I(b):

A phenethyl halide is reacted with an alkyl nitrile in the presence of stannic chloride or sulfur chloride cyclizing agent to form a dihydroisoquinoline intermediate.

Step II:

The dihydroisoquinoline intermediate is reduced to a 1-substituted-1,2,3,4-tetrahydroisoquinoline. Reduction may occur by hydrogenation in the presence of a noble metal catalyst or by use of a borohydride compound.

Step III:

The resulting isoquinoline intermediate is then reacted with an acylating agent to provide a haloacyl 1-substituted-1,2,3,4-tetrahydroisoquinoline.

The following examples are presented for illustrative purposes only and are not intended as a restriction on the scope of the invention. All parts are by weight unless otherwise indicated. Most of the commercially-available starting materials were obtained from Aldrich Chemical Co., Milwaukee, Wis. Table I sets forth analytical data for specific compounds prepared in accordance with the procedures of Examples 1-21.

EXAMPLE 1

(Method A)

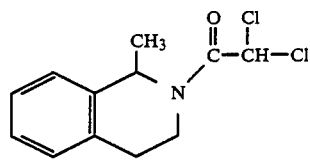

2-(Dichloroacetyl)-1-methyl-1,2,3,4-tetrahydroisoquinoline

A reaction vessel was charged with 0.1 mol phenethylamine, 100 ml methylene chloride and 50 ml 10% sodium hydroxide. With this mixture at room temperature, 0.11 mol acetyl chloride was added dropwise to the reaction mixture. Then, water was added to the reaction vessel, and the aqueous phase was separated from the organic phase. The organic phase was dried with magnesium sulfate and stripped of solvent providing an amide-containing intermediate product. To this intermediate product was added phosphorus pentoxide and 100 ml phosphorus oxychloride. The mixture was refluxed overnight, then poured into an ice. With the mixture cooled in ice, the mixture was made alkaline with sodium hydroxide. The mixture was extracted with ethyl ether, then the extract was dried with magnesium sulfate and stripped of solvent. The residue was distilled (62° C. @ 0.25 mm Hg) to provide 9 g of a yellow oil product identified as containing 1-methyl-1,2,3,4-tetrahydroisoquinoline (62% yield). A reaction vessel was charged with 9 g of this yellow oil product, 1.17 g sodium borohydride and 80 ml methanol. The mixture was refluxed for three hours. Then, 5 ml 10% sodium hydroxide was stirred into the mixture, followed by addition of 20 ml water. Methanol was stripped from the mixture, water was added, and then the mixture was extracted with methylene chloride. The extract was dried with magnesium sulfate, stripped of solvent, and then distilled to provide 7.4 g of a yellow oil. A reaction vessel was charged with 3 g of this yellow oil, 2.15 ml dichloroacetyl chloride and 20 ml toluene. The reaction mixture was refluxed for one hour, cooled, stripped of solvent, and subjected to Kugelrohr distillation (120° C. @ 0.01 mm Hg) to provide 3 g of a yellow oil product having the elemental analysis reported in Table I.

EXAMPLE 1

(Method B)

A reaction vessel was charged with 2723 ml acetonitrile which was held under a nitrogen blanket. With the reaction vessel cooled in an ice bath, 1888.5 g stannic chloride was added gradually below the surface of the acetonitrile with stirring over a period of 2 hours 20 minutes. During the addition period, the temperature of the reaction mixture varied between 3° C. and 39° C. The mixture was allowed to stand overnight at room temperature. With the reaction mixture at 22° C., 916 g 2-chloroethylbenzene was added in increments to the reaction vessel over a ten-minute period. With the mixture under reduced pressure and heated, 1369.7 g acetonitrile was gradually stripped from the mixture. During the stripping period, the temperature of the mixture varied from 23° C. to 84° C. and the pressure in the reaction vessel varied from 45 mm Hg to about 100 mm Hg. The reaction mixture, milky in color, was heated to reflux. The reaction mixture was maintained at reflux for about 6½ hours during which period the temperature of the mixture varied from about 109° C. to about 113° C. With the temperature of the reaction mixture at about 75° C., the entire amount of previously-stripped acetonitrile was added back to the reaction mixture. The mixture was allowed to cool, stand overnight and was observed to contain a slurry. About 2 liters of methylene chloride was added to the mixture. Then, this mixture was added with stirring to 4 liters of 10% sodium hydroxide previously cooled to about 10° C. The temperature of the mixture reached 40° C. and the mixture was found to be acidic. About 13 liters more 10% sodium hydroxide was added to make the mixture alkaline. The organic phase was separated and washed with water. The organic phase was dried over sodium sulfate, filtered and stripped on a rotary evaporator at a temperature of 35°-40° C. to provide 749.3 g 1-methyl-3,4-dihyroisoquinoline (79.2% yield based on 2-chloroethylbenzene starting material). An autoclave was charged with a slurry of 300 g 50%-wetted 5% palladium-on-carbon catalyst in 8 liters absolute ethanol. Then, there was added to the slurry a mixture of 2143.2 g 1-methyl-3,4-dihydroisoquinoline along with 82.2 g 2-chloroethylbenzene contaminant (such as prepared by the foregoing procedures). The autoclave was flushed with hydrogen gas. With the reaction mixture being stirred, the autoclave was gradually pressurized with hydrogen over a period of about two hours to a final pressure of about 185 psi (12.5 atm; $12.6 \times 10^5$ Pascal) and temperature of about 50° C. The autoclave was maintained in this pressurized condition overnight. The temperature of the autoclave dropped to 9° C. after venting with stirring of the reaction mixture. The mixture was filtered and stripped of ethanol to provide 2100.0 g 1-methyl-1,2,3,4-tetrahydroisoquinoline (96.7% based on 1-methyl-3,4-di-hydroisoquinoline starting material). A reaction vessel was charged with a mixture of 1136 g 1-methyl-1,2,3,4-tetrahydroisoquinoline in 1360 ml toluene. The mixture was cooled to 10° C., stirred and placed under a nitrogen blanket. With the temperature of the mixture at 10° C., 150 ml dichloroacetyl chloride was added to the reaction mixture gradually in a 13-minute period, after which time the temperature reached 70° C. Then, over a two-hour period portions of dichloroacetyl chloride and toluene were added gradually until a total of 780 ml dichloroacetyl chloride and 2100 ml toluene were added. The mixture was heated to reflux over a 2½ hour period during which time HCl gas evolved from the reaction mixture. The mixture was cooled and 100 g silica gel was added to the mixture. The mixture was filtered and then stripped of toluene and of excess dichloroacetyl chloride to provide 1801.5 g 2-(dichloroacetyl)-1-methyl-1,2,3,4-tetrahydroisoquinoline (97.7% yield based on 1-methyl-1,2,3,4-tetrahydroisoquinoline starting material).

EXAMPLE 2

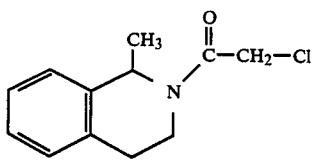

2-(2-Chloroacetyl)-1-methyl-1,2,3,4-tetrahydroisoquinoline

A reaction vessel was charged with 50 ml toluene and 2 g 1-methyl-1,2,3,4-tetrahydroisoquinoline (prepared by procedure of Example 1,—Method A). Then, 2 ml 2-chloroacetyl chloride was added gradually to the mixture. The reaction mixture was stirred and heated until a homogeneous solution appeared. The mixture was filtered, stripped of solvent, and subjected to Kugelrohr distillation 130° C. @ 0.2 mm Hg) to provide 2.7 g of an amber oil product having the elemental analysis reported in Table I.

EXAMPLE 3

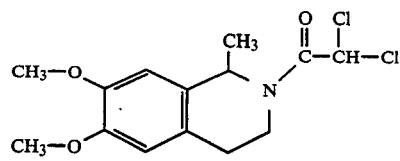

2-(Dichloroacetyl)-1-methyl-6,7-dimethoxy-1,2,3,4-tetrahydro-isoquinoline

A reaction vessel was charged with 0.1 mol 3,4-dimethoxyphenethylamine, 40 ml 10% sodium hydroxide and 100 ml methylene chloride. With stirring of this mixture, 0.11 mol acetyl chloride was added dropwise. The mixture was then stirred for two minutes and water was added. The methylene chloride extract was dried with magnesium sulfate and stripped of solvent. The residue, washed with hot cyclohexane and hot n-heptane, provided 14 g of a yellow solid having a melting point of 91°-92° C. A reaction vessel was charged with 10 g of this yellow solid, 10 g phosphorus pentoxide and 50 ml phosphorus oxychloride. The mixture was refluxed overnight and then poured into 1000 ml of ice. After cooling, the mixture was made alkaline with sodium hydroxide and then extracted with ethyl ether. The ether extract was dried over magnesium sulfate, stripped of solvent, and then the product was recrystallized from cyclohexane. About 4 g of this product was placed in a reaction vessel along with 0.74 g sodium borohydride and 50 ml methanol. The reaction mixture was refluxed for 4 hours. Then, 5 ml 10% sodium hydroxide was added and the mixture stirred for 5 minutes. Solvent was stripped from the mixture and then methylene chloride and water were added to the mixture. The organic extract was dried with magnesium sulfate, stripped of solvent and then subjected to Kugelrohr distillation (130° C. @ 0.25 mm Hg). About 3 g of this distillate was placed in a reaction vessel with 1.5 ml dichloroacetyl chloride and 25 ml toluene. The reaction mixture was refluxed until a clear solution appeared. Solvent was stripped from the mixture, then the residue was dried under reduced pressure with heat using a 70°

C. water bath. A viscous, yellow oil product was recovered having the elemental analysis reported in Table I.

EXAMPLE 4

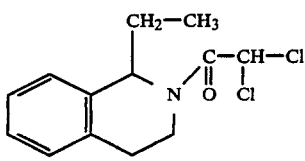

2-(Dichloroacetyl)-1-ethyl-1,2,3,4-tetrahydroisoquinoline

By procedures described in Example 1 (Method A), phenethylamine and propionyl chloride were converted to 1-ethyl-1,2,3,4-tetrahydroisoquinoline. A reaction vessel was charged with 2.5 g of this isoquinoline compound in 50 ml toluene. With this mixture stirred, 1.5 ml dichloroacetyl chloride was added dropwise to the mixture. The mixture was refluxed until a clear solution appeared. The mixture was stripped of solvent and subjected to Kugelrohr distillation (150° C. @ 0.25 mm Hg) to provide 2.7 g of product having the elemental analysis reported in Table I.

EXAMPLE 5

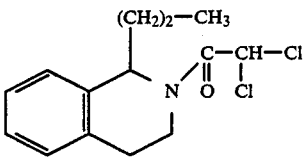

2-(Dichloroacetyl)-1-n-propyl-1,2,3,4-tetrahydroisoquinoline

By procedures described in Example 1, (Method A), phenethylamine and n-butyryl chloride were converted to 1-n-propyl-1,2,3,4-tetrahydroisoquinoline. A reaction vessel was charged with 2.0 g of this isoquinoline compound, 10 ml 10% sodium hydroxide and 50 ml methyl chloride. With this mixture stirred, 2 ml dichloroacetyl chloride was added dropwise to the mixture. The mixture was stirred for 2 minutes, then water was added. The organic extract was dried with magnesium sulfate, stripped of solvent and subjected to Kugelrohr distillation (150° C. @ 0.25 mm Hg) to provide 3.5 g of a viscous yellow oil product having the elemental analysis reported in Table I.

EXAMPLE 6

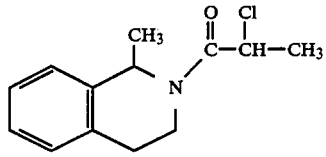

2-(2-chloropropionyl)-1-methyl-1,2,3,4-tetrahydroisoquinoline

A reaction vessel was charged with 50 ml toluene and 2.0 g 1-methyl-1,2,3,4-tetrahydroisoquinoline (prepared by procedure of Example 1—Procedure A). Then, 2.0 ml 2-chloropropionyl chloride was added gradually to the mixture. The reaction mixture was stirred and heated until a homogeneous solution appeared. The mixture was filtered, stripped of solvent, and subjected to Kugelrohr distillation (150° C. @ 0.25 mm Hg) to provide 2.8 g of a yellow oil product having the elemental analysis reported in Table I.

EXAMPLE 7

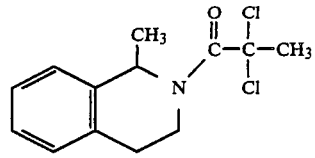

2-(2,2-dichloropropionyl)-1-methyl-1,2,3,4-tetrahydroisoquinoline

A reaction vessel was chrged with 2 g 1-methyl-1,2,3,4-tetrahydroisoquinoline, 10 ml 10% sodium hydroxide and 50 ml methylene chloride. With this mixture stirred, 3 ml 2,2-dichloropropionyl chloride was added dropwise to the mixture. The mixture was stirred for 20 minutes, then water was added. The organic extract was dried with magnesium sulfate, stripped of solvent and subjected to Kugelrohr distillation (170° C. @ 0.25 mm Hg) to provide 2.7 g of a yellow oil product having the elemental analysis reported in Table I.

EXAMPLE 8

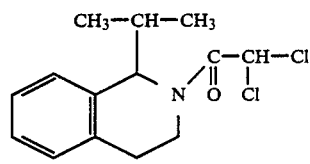

2-(Dichloroacetyl)-1-(1-methylethyl)-1,2,3,4-tetrahydroisoquinoline

A reaction vessel was charged with 0.1 mol β-phenethylamine, 50 ml 10% sodium hydroxide, and 100 ml methylene chloride. With stirring of this mixture, 0.11 mol isobutyryl chloride was added dropwise. The reaction mixture was stirred for about 2 minutes. Water was added. The organic phase separated and then was dried with magnesium sulfate. Solvent was stripped from the organic phase and the residue was recrystallized from cyclohexane to provide white leaflet-like crystal product (95% yield). To 15 g of this product there were added 100 ml phosphorus oxychloride and 20 g phosphorus pentoxide. The reaction mixture was refluxed overnight, then poured into ice, and made alkaline to pH 7-8 with ammonium hydroxide. With the mixture cooled with ice, the mixture was extracted with methylene chloride. The extract was dried with magnesium sulfate, stripped of solvent, and then subjected to Kugelrohr distillation (100° C. @ 0.11 mm Hg) to provide 13 g of a clear oil. To 10 g of this clear oil there was added 1.5 g sodium borohydride and 50 ml methanol. The reaction mixture was stirred for 2 hours and then 10 ml 10% sodium hydroxide solution was added. The mixture was then stirred for 2 minutes, stripped of solvent, and then extracted with methylene chloride and water. The organic phase was dried with magnesium sulfate, stripped of solvent, and then subjected to Kugelrohr distillation (100° C. @ 0.1 mm Hg) to provide 9 g of a yellow oil. To 4.7 g of this yellow oil there was added 4 ml dichloroacetyl chloride, 10 ml 10% sodium hydroxide and 50 ml methylene chloride. The reaction mixture was stirred for 2 minutes, water was added and the organic extract was dried with magnesium sulfate. The dried extract was stripped of solvent and then subjected to Kugelrohr distillation (100° C. @ 0.025 mm Hg) to provide 3.8 g of a viscous yellow oil product having the elemental analysis reported in Table I.

EXAMPLE 9

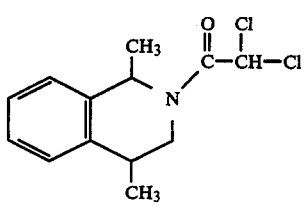

2-(Dichloroacetyl)-1,4-dimethyl-1,2,3,4-tetrahydroisoquinoline

A reaction vessel was charged with 21 g β-methyl-phenethylamine, 62 ml 10% sodium hydroxide, and 100 ml methylene chloride. With stirring of this mixture, 13 ml acetyl chloride in 50 ml methylene chloride was added dropwise. The reaction mixture was stirred for 10 minutes. Water was added and the methylene chloride separated, which was dried with magnesium sulfate stripped of solvent, and then concentrated under reduced pressure to provide 24 g of a yellow oil. To 20 g of this yellow oil there was added 50 ml phosphorus oxychloride and 20 g phosphorus pentoxide. The reaction mixture was refluxed for 6 hours, cooled, and stripped of excess phosphorus oxychloride. Toluene was added to the mixture, then solvent stripped from the mixture, and then the toluene-stripping step was repeated. Water was added to the mixture, then the mixture was made alkaline with sodium hydroxide. The mixture was extracted with methylene chloride, the organic phase was stripped of solvent and the residue was subjected to Kugelrohr distillation (50° C. @ 0.01 mm Hg) to provide 10 g of a clear oil. To this clear oil there were added a catalytic amount of 10% palladium-on-carbon catalyst and 20 ml ethanol. Hydrogenation was carried out in a Parr shaker for about 3 hours under 3 atmospheres. The catalyst was removed by filtration, the filtrate stripped of solvent, and the residue subjected to Kugelrohr distillation (100° C. @ 0.1 mm Hg) to provide 10 g of a clear oil. To 3 g of this clear oil there was added 2 ml dichloroacetyl chloride, 10 ml 10% sodium hydroxide and 50 ml methylene chloride. The reaction mixture was stirred for 2 minutes, water was added and the organic extract was dried with magnesium sulfate. The dried extract was stripped of solvent and then subjected to Kugelrohr distillation 150° C. @ 0.25 mm Hg) to provide a product having the elemental analysis reported in Table 1.

EXAMPLE 10

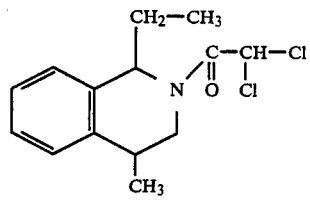

2-(Dichloroacetyl)-1-ethyl-4-methyl-1,2,3,4-tetrahydroisoquinoline

By procedures described in Example 1 (Method A), β-methyl-phenethylamine and propionyl chloride were converted to 1-ethyl-4-methyl-1,2,3,4-tetrahydroisoquinoline. A reaction vessel was charged with 8 g of this isoquinoline compound, 10 ml 10% sodium hydroxide and 50 ml methylene chloride. With this mixture stirred, 1.1 equivalents dichloroacetyl chloride was added dropwise to the mixture. The mixture was stirred for 2 minutes, then water was added. The organic extract was dried with magnesium sulfate and stripped solvent. The residue was recrystallized from cyclohexane to provide 4 g of a white solid product having the elemental analysis reported in Table I.

EXAMPLE 11

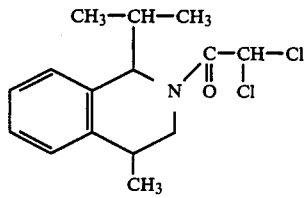

2-(Dichloroacetyl)-1-(1-methylethyl)-4-methyl-1,2,3,4-tetrahydro-isoquinoline

By procedures described in Example 1 (Method A), β-methyl-phenethylamine and isobutyryl chloride were converted to -4-methyl-1,2,3,4-tetrahydroisoquinoline. A reaction vessel was charged with 3.0 g of this isoquinoline compound, 10 ml 10% sodium hydroxide and 50 ml methylene chloride. With this mixture stirred, 2 ml dichloroacetyl chloride was added dropwise to the mixture. The mixture was stirred for 2 minutes, then water was added. The organic extract was dried with magnesium sulfate and stripped of solvent. The residue was recrystallized from aqueous ethanol to provide 4 g of a white needle-crystalline product having the elemental analysis reported in Table I.

EXAMPLE 12

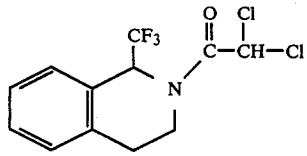

2-(Dichloroacetyl)-1-trifluoromethyl-1,2,3,4-tetrahydroisoquinoline

By procedures described in Example 1 (Method A), phenethylamine and trifluoroacetyl chloride were converted to 1-trifluoromethyl-1,2,3,4-tetrahydroisoquinoline. A reaction vessel was charged with 3.5 g of this isoquinoline compound, 20 ml 10% sodium hydroxide and 50 ml methylene chloride. With this mixture stirred, 2 ml dichloroacetyl chloride was added dropwise to the mixture. The mixture was stirred for 2 minutes, then water was added. The organic extract was dried with magnesium sulfate, stripped of solvent, and subjected to Kugelrohr distillation (130° C. @ 0.1 mm Hg) to provide a product having the elemental analysis reported in Table I.

EXAMPLE 13

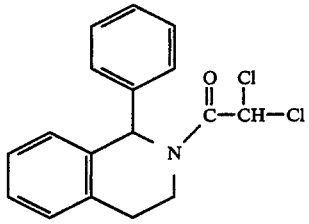

2-(Dichloroacetyl)-1-phenyl-1,2,3,4-tetrahydroisoquinoline

By procedures described in Example 1 (Method A), phenethylamine and benzoyl chloride were converted to 1-phenyl-1,2,3,4-tetrahydroisoquinoline. A reaction vessel was charged with 3.5 g of this isoquinoline compound, 10 ml 10% sodium hydroxide and 50 ml methylene chloride. With this mixture stirred, 1.2 ml dichloroacetyl chloride was added dropwise to the mixture. The mixture was stirred for 10 minutes, then water was added. The organic extract was dried with magnesium sulfate and stripped of solvent. The residue was recrystallized from ethanol to provide 4 g of a white cubic-crystal product having the elemental analysis reported in Table I.

EXAMPLE 14

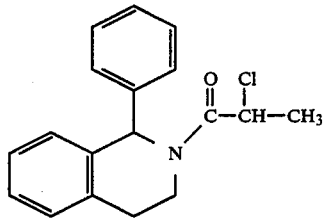

2-(2-chloropropionyl)-1-phenyl-1,2,3,4-tetrahydroisoquinoline

By procedures described in Example 1 (Method A), phenethylamine and benzoyl chloride were converted to 1-phenyl-1,2,3,4-tetrahydroisoquinoline. A reaction vessel was charged with 3.0 g of this isoquinoline compound, 5 ml 10% sodium hydroxide and 50 ml methylene chloride. With this mixture stirred, 1 ml 2-chloropropionyl chloride was added dropwise to the mixture. The mixture was stirred for 10 minutes, then water was added. The organic extract was dried with magnesium sulfate, stripped of solvent and subjected to Kugelrohr distillation (170° C. @ 0.1 mm Hg) to provide 2.3 g of a viscous yellow oil product having the elemental analysis reported in Table I.

EXAMPLE 15

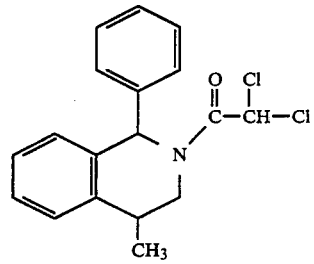

2-(Dichloroacetyl)-1-phenyl-4-methyl-1,2,3,4-tetrahydroisoquinoline

By procedures described in Example 1 (Method A), β-methyl-phenethylamine and benzoyl chloride were converted to 4-methyl-1,2,3,4-tetrahydroisoquinoline. A reaction vessel was charged 4-methyl-1-phenyl-1,2,3,4-tetrahydroisoquinoline. A reaction vessel was charged with 3.0 g of this isoquinoline compound, 5 ml 10% sodium hydroxide and 50 ml methylene chloride. With this mixture stirred, 2 ml dichloroacetyl chloride was added dropwise to the mixture. The mixture was stirred for 5 minutes, then water was added. The organic extract was dried with magnesium sulfate, stripped of solvent and subjected to Kugelrohr distillation (160° C. @ 0.1 mm Hg) to provide 4 g of a yellow oil product having the elemental analysis reported in Table I.

EXAMPLE 16

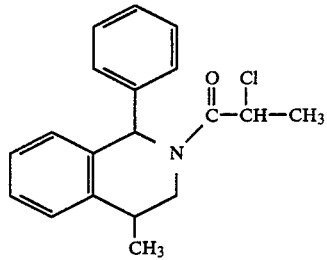

2-(2-Chloro-1-oxopropyl)-1-phenyl-4-methyl-1,2,3,4-tetrahydro-isoquinoline

By procedures described in Example 1 (Method A), β-methyl-phenethylamine and benzoyl chloride were converted to 4-methyl-1,2,3,4-tetrahydroisoquinoline. A reaction vessel was charged with 4.0 g of this isoquinoline compound, 10 ml 10% sodium hydroxide and 50 ml methylene chloride. With this mixture stirred, 2 ml 2-chloropropionyl chloride was added dropwise to the mixture. The mixture was stirred for 15 minutes, then water was added. The organic extract was dried with magnesium sulfate, stripped of solvent and subjected to Kugelrohr distillation (150° C. @ 0.1 mm Hg)

EXAMPLE 17

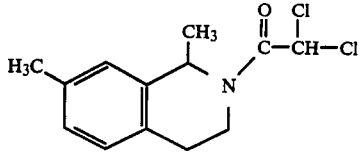

2-(Dichloroacetyl)-1,7-dimethyl-1,2,3,4-tetrahydroisoquinoline

A reaction vessel was charged with 5 g 4(2-chloroethyl)toluene, 5 ml stannic chloride and 50 ml acetonitrile. The reaction mixture was refluxed for 4 hours, cooled and then poured into water. The mixture was extracted with ethyl ether and the aqueous layer was separated. Ice was added to the aqueous portion which was then made alkaline with 50% sodium hydroxide. The alkaline aqueous solution was extracted with methylene chloride, and the organic extract was dried with magnesium sulfate and stripped of solvent to provide 2.7 g of a yellow oil. To this yellow oil there was added 2 g sodium borohydride and 50 ml ethanol. The reaction mixture was refluxed for 4 hours, cooled, and then 20 ml 10% sodium hydroxide was added. Solvent was stripped from the mixture, then water and methylene chloride were added. The organic extract was dried with magnesium sulfate and stripped of solvent to provide 4 g of a clear oil. To 4 g of this clear oil there was added 4 ml dichloroacetyl chloride and 50 ml methylene chloride. The reaction mixture was stirred for 20 minutes, then made alkaline with 20 ml 10% sodium hydroxide. The organic portion was dried with magnesium sulfate and stripped of solvent to provide 3.5 g of a yellow oil having the elemental analysis reported in Table I.

EXAMPLE 18

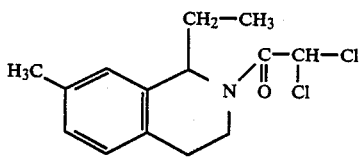

2-(Dichloroacetyl)-1-ethyl-7-methyl-1,2,3,4-tetrahydroisoquinoline

By procedures described in Example 1 (Method A), 4-methyl-phenethylamine and propionyl chloride were converted to 1-ethyl-7-methyl-1,2,3,4-tetrahydroisoquinoline. A reaction vessel was charged with 3.0 g of this isoquinoline compound, 10 ml 10% sodium hydroxide and 50 ml methylene chloride. With this mixture stirred, 2 ml dichloroacetyl chloride was added dropwise to the mixture. The mixture was stirred for 5 minutes and then made alkaline with aqueous sodium hydroxide. The organic extract was dried with magnesium sulfate, stripped of solvent and subjected to Kugelrohr distillation (105° C. @ 0.1 mm Hg) to provide 4.8 g of a yellow oil product having the elemental analysis reported in Table I.

EXAMPLE 19

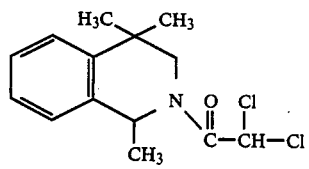

2-(Dichloroacetyl)-1,4,4-trimethyl-1,2,3,4-tetrahydroisoquinoline

By procedures described in Example 1 (Method B), 1-chloro-2-methyl-2-phenyl-propane and acetonitrile were converted to 1-methyl-4,4-dimethyl-1,2,3,4-tetrahydroisoquinoline. A reaction vessel was charged with 4.0 g of this isoquinoline compound and 50 ml methylene chloride. With this mixture stirred, 2 ml dichloroacetyl chloride was added dropwise to the mixture. The mixture was stirred for 20 minutes and then made alkaline with aqueous sodium hydroxide. The organic extract was dried with magnesium sulfate and stripped of solvent. The residue was recrystallized from ethanol to provide 4.2 g of a white cubic-crystal product having the elemental analysis reported in Table I.

EXAMPLE 20

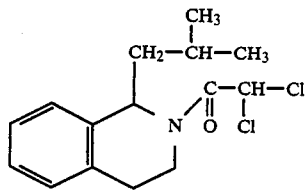

2-(Dichloroacetyl)-1-(2,2-dimethylethyl)-1,2,3,4-tetrahydroisoquinoline

A reaction vessel was charged with 0.1 mol phenethyl chloride, 0.15 mol stannic chloride and 40 ml isobutyronitrile. The reaction mixture was refluxed overnight. Water was added, the mixture was cooled, and then ethyl ether was added. The aqueous portion was separated, made alkaline with ammonium hydroxide, and then extracted with ethyl ether. The ether extract was dried with magnesium sulfate, and then stripped of solvent to give 8.5 g of a yellow oil. To 8.5 g of this yellow oil there was added 2 g sodium borohydride and 50 ml ethanol. The reaction mixture was refluxed overnight, then 20 ml 10% sodium hydroxide was added, and solvent was stripped from the mixture. Water and ethyl ether were added to the residue, then the organic extract was dried with magnesium sulfate and stripped of solvent to provide a yellow oil. To 8 g of this yellow oil there was added 6 ml of dichloroacetyl chloride and 100 ml methylene chloride. The reaction mixture was stirred for 20 minutes, then water was added, and the organic extract was dried with magnesium sulfate. The organic extract was stripped of solvent and subjected to Kugelrohr distillation (140° C. @ 0.1 mm Hg) to give 10.0 g of a yellow oil product having the elemental analysis reported in Table I.

EXAMPLE 21

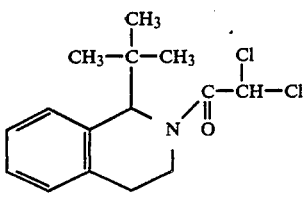

2-(Dichloroacetyl)-1-(1,1-dimethylethyl)-1,2,3,4-tetrahydroisoquinoline

A reaction vessel was charged with 0.2 mol phenethyl chloride, 50 ml 2,2-dimethylpropionitrile and 15 ml stannic chloride. The reaction mixture was refluxed overnight, cooled, and water added. The aqueous extract was made alkaline with ammonium hydroxide, then extracted with ethyl ether. The organic extract was dried with magnesium sulfate and stripped of solvent to provide 1 g of a yellow oil. To 1 g of this yellow oil there was added 0.5 g sodium borohydride and 25 ml ethanol. The reaction mixture was refluxed overnight, cooled, and then 40 ml 10% sodium hydroxide was added. Water was added to the mixture and then ethanol was stripped from the mixture. Methylene chloride was added to the mixture. The organic extract was dried with magnesium sulfate and then stripped of solvent to provide 0.8 g of a yellow oil to of this yellow oil there was added 1 ml of dichloroacetyl chloride and 50 ml methylene chloride. The mixture was stirred for 20 minutes and then 50 ml 10% sodium hydroxide was added. The organic extract was dried with magnesium sulfate, stripped of solvent, and then subjected to Kugelrohr distillation (150° C. @ 0.1 mm Hg) to provide 0.5 g of a yellow oil product having the elemental analysis reported in Table I.

EXAMPLE 22

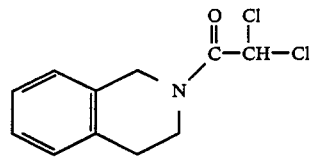

2-(Dichloroacetyl)-b 1,2,3,4-tetrahydroisoquinoline

A reaction vessel was charged with 13.4 g (0.1 mol) 1,2,3,4-tetrahydro-isoquinoline and 90 ml toluene. Then, 15.3 g (0.105 mol) dichloroacetyl chloride was added dropwise to the mixture. The reaction mixture was heated at reflux for 10 hours. The mixture was stripped of solvent and crystal product formed. The crystal product was filtered, the filter cake was washed with cyclohexane, and the crystal product was air-dried to provide 10.5 g of product having a melting point of 84°–86° C. and the following elemental analysis:

|      | Theory | Found |
|------|--------|-------|
| % C  | 54.12  | 54.12 |
| % H  | 4.54   | 4.54  |
| % Cl | 29.05  | 28.97 |

BIOLOGICAL EVALUATION

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in

TABLE I

| Example Compound No. | Empirical Formula | Molecular Weight | % C Theory | % C Found | % H Theory | % H Found | % N*/Cl**/F*** Theory | Found |
|---|---|---|---|---|---|---|---|---|
| 1 | $C_{12}H_{13}Cl_2NO$ | 258.15 | 55.83 | 55.50 | 5.08 | 5.26 | 5.43 | 5.21* |
| 2 | $C_{12}H_{14}ClNO$ | 223.70 | 64.43 | 64.28 | 6.31 | 6.36 | 6.26 | 6.10* |
| 3 | $C_{14}H_{17}Cl_2NO_3$ | 318.20 | 52.85 | 52.46 | 5.39 | 5.35 | 4.40 | 4.22* |
| 4 | $C_{13}H_{15}Cl_2NO$ | 272.18 | 57.37 | 57.27 | 5.56 | 5.59 | 5.15 | 5.10* |
| 5 | $C_{14}H_{17}Cl_2NO$ | 286.20 | 58.75 | 58.65 | 5.99 | 6.01 | 4.89 | 4.86* |
| 6 | $C_{13}H_{16}ClNO$ | 237.73 | 65.68 | 65.87 | 6.78 | 6.76 | 5.89 | 5.83* |
| 7 | $C_{13}H_{15}Cl_2NO$ | 272.18 | 57.37 | 57.61 | 5.56 | 5.66 | 5.15 | 5.22* |
| 8 | $C_{14}H_{17}Cl_2NO$ | 286.20 | 58.75 | 59.00 | 5.99 | 6.30 | 4.89 | 5.14* |
| 9 | $C_{13}H_{15}Cl_2NO$ | 272.18 | 57.37 | 57.38 | 5.56 | 5.60 | 5.15 | 5.12* |
| 10 | $C_{14}H_{17}Cl_2NO$ | 286.20 | 58.75 | 58.63 | 5.99 | 6.16 | 4.89 | 5.07* |
| 11 | $C_{15}H_{19}Cl_2NO$ | 300.23 | 60.01 | 60.03 | 6.38 | 6.08 | 4.67 | 4.41* |
| 12 | $C_{12}H_{10}Cl_2F_3NO$ | 312.12 | 46.18 | 46.30 | 3.23 | 3.27 | 4.49 | 4.49* |
|   |   |   |   |   |   |   | 22.72 | 22.64** |
| 13 | $C_{17}H_{15}Cl_2NO$ | 320.22 | 63.76 | 63.64 | 4.72 | 4.73 | 4.37 | 4.35* |
| 14 | $C_{18}H_{18}ClNO$ | 299.80 | 72.11 | 71.13 | 6.05 | 6.09 | 4.67 | 4.63* |
| 15 | $C_{18}H_{17}Cl_2NO$ | 334.25 | 64.68 | 64.55 | 5.13 | 5.27 | 4.19 | 4.42* |
| 16 | $C_{19}H_{20}NO$ | 313.83 | 72.72 | 72.70 | 6.42 | 6.51 | 4.46 | 4.65* |
| 17 | $C_{13}H_{15}Cl_2NO$ | 272.18 | 57.37 | 57.47 | 5.56 | 5.63 | 5.15 | 5.09* |
| 18 | $C_{14}H_{17}Cl_2NO$ | 286.20 | 58.75 | 58.79 | 5.99 | 6.02 | 4.89 | 4.87* |
| 19 | $C_{14}H_{17}Cl_2NO$ | 286.20 | 58.75 | 58.80 | 5.99 | 6.01 | 4.89 | 4.89* |
| 20 | $C_{15}H_{19}Cl_2NO$ | 300.23 | 60.01 | 58.83 | 6.38 | 6.01 | 4.67 | 5.02* |
| 21 | $C_{15}H_{19}Cl_2NO$ | 300.23 | 60.01 | 60.09 | 6.38 | 6.44 | 4.67 | 4.67* | combination". Or, the soil may be treated with the herbicide and antidote compounds separately so that the "combination" is made on, or in, the soil. After such treatments of the soil, with a mixture of herbicide and antidote, or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as "combination" is a commercially-convenient of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-50:1 (preferably 1:5-to 30:1) parts by weight may be employed. As indicated above, the antidote may be applied to the plant locus in a mixture, i.e., a mixture of a herbicidally-effective amount of herbicide and a safening-effective amount of an antidote or sequentially, i.e., the plant locus may be treated with an effective amount of the herbicide followed by a treatment with the antidote or vice versa. In general, effective herbicidal amounts are in the range of about 0.1 to about 12 kilograms/hectare. The preferred range of rate of application is from about 0.4 to about 10 Kg/h. Preferably, antidote application rates range from about 0.5 Kg/ha down to about 0.05 Kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples 23-25 in greenhouse testing. Measurements of biological response as reported in Tables II-IV were made in the following manner. A visual comparison was made between a crop plant treated with herbicide alone and crop plant having no herbicide or antidote treatment. A number was assigned to this visual comparison indicating the percent injury or inhibition to the herbicide-alone treated crop plant (column "WO" in Tables II-IV indicating herbicide "without" antidote). Also, a visual comparison was made between the crop plant treated with herbicide+antidote combination and the crop plant having no herbicide or antidote treatment. A number was assigned to this visual comparison indicating the percent injury or inhibition to the herbicide+antidote treated crop plant (column "W" in Tables II-IV indicating herbicide "with" antidote). Where treatments involved weed plant species, observations of response to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables II-IV are data showing "safening effect" for the herbicide+antidote combinations calculated from the plant inhibition numbers.

Summarized below is key information for interpreting data reported in Tables II-IV:

| Herbicide No. | Name |
|---|---|
| 1 | 2,3,3-trichloroallyldiisopropylthiocarbamate (triallate) |
| 2 | 2-chloro-4-ethylamine-6-isopropylamino-1,3,5-triazine (atrazine) |
| 3 | 2-chloro-2',6'-diethyl-N—(methoxymethyl)-acetanilide (alachlor) |
| 4 | 2-chloro-2'6'-diethyl-N—(butoxymethyl)-acetanilide (butachlor) |
| 5 | 2-chloro-N—(ethoxymethyl)-6'-ethyl-o-acetotoluidide (acetochlor) |
| 6 | 2-chloro-2'-methyl-6'-methoxy-N—(isopropoxymethyl)acetanilide |

Antidote No. = Compound in corresponding Example No.
Rate = kilograms/hectare (Kg/ha).
W = % Plant Inhibition caused by combination of herbicide and antidote.
WO = % Plant Inhibition caused by herbicide alone.
Data reported in parentheses = % Safening Effect
$$(\text{———}) = \frac{WO - W}{WO} \times 100$$

EXAMPLE 23

The following procedure shows interaction between a herbicide and antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded furrows of the third container. Antidote application rate was 0.55 mg active compound per inch of furrow. This rate was comparable to a plot application rate of 0.28 kilogram per hectare (kg/ha), based on 76 cm (30") spaced-apart furrows. Then, each of the second and third containers was filled and leveled with a cover layer of soil having incorporated therein the selected herbicide at a pre-determined concentration. The first container was filled and leveled with soil containing no herbicide. The containers were then placed on a greenhouse bench and sub-irrigated as required for the duration of the test. Plant response was observed about three weeks after initial treatment. Results are reported in Table II.

TABLE II

| HERBICIDE | | ANTIDOTE | | \% PLANT INHIBITION AND \% SAFENING EFFECT ( ) | | | | | | | | | |
|---|---|---|---|---|---|---|---|---|---|---|---|---|---|
| | | | | SORGHUM | | WHEAT | | RICE | | SOYBEAN | | CORN | |
| No. | RATE | No. | RATE | W | WO | W | WO | W | WO | W | WO | W | WO |
| 1 | 0.56 | 1 | 0.28 | | | 90 | 95 | | | | | | |
| | | | | | | (5) | | | | | | | |
| 1 | 0.56 | 2 | 0.28 | | | 100 | 100 | | | | | | |
| | | | | | | (0) | | | | | | | |
| 1 | 0.56 | 3 | 0.28 | | | 95 | 100 | | | | | | |
| | | | | | | (5) | | | | | | | |
| 1 | 0.56 | 4 | 0.28 | | | 90 | 95 | | | | | | |
| | | | | | | (5) | | | | | | | |
| 1 | 0.56 | 5 | 0.28 | | | 95 | 100 | | | | | | |
| | | | | | | (5) | | | | | | | |
| 1 | 0.56 | 6 | 0.28 | | | 90 | 100 | | | | | | |
| | | | | | | (10) | | | | | | | |
| 1 | 0.56 | 7 | 0.28 | | | 95 | 100 | | | | | | |
| | | | | | | (5) | | | | | | | |
| 1 | 0.56 | 8 | 0.28 | | | 85 | 100 | | | | | | |
| | | | | | | (15) | | | | | | | |
| 1 | 0.56 | 9 | 0.28 | | | 40 | 95 | | | | | | |
| | | | | | | (57) | | | | | | | |
| 1 | 0.56 | 10 | 0.28 | | | 75 | 100 | | | | | | |
| | | | | | | (25) | | | | | | | |
| 1 | 0.56 | 11 | 0.28 | | | 90 | 95 | | | | | | |
| | | | | | | (5) | | | | | | | |
| 1 | 0.56 | 12 | 0.28 | | | 85 | 95 | | | | | | |
| | | | | | | (10) | | | | | | | |
| 1 | 0.56 | 13 | 0.28 | | | 100 | 95 | | | | | | |
| | | | | | | (0) | | | | | | | |
| 1 | 0.56 | 14 | 0.28 | | | 90 | 95 | | | | | | |
| | | | | | | (5) | | | | | | | |
| 1 | 0.56 | 15 | 0.28 | | | 40 | 90 | | | | | | |
| | | | | | | (55) | | | | | | | |
| 1 | 0.56 | 16 | 0.28 | | | 30 | 90 | | | | | | |
| | | | | | | (66) | | | | | | | |
| 1 | 0.56 | 17 | 0.28 | | | 95 | 95 | | | | | | |
| | | | | | | (0) | | | | | | | |
| 1 | 0.56 | 18 | 0.28 | | | 85 | 95 | | | | | | |
| | | | | | | (10) | | | | | | | |
| 1 | 0.56 | 19 | 0.28 | | | 95 | 95 | | | | | | |
| | | | | | | (0) | | | | | | | |
| 2 | 4.48 | 1 | 0.28 | | | | | 60 | 60 | | | 100 | 95 |
| | | | | | | | | (0) | | | | (0) | |
| 2 | 4.48 | 2 | 0.28 | | | | | 95 | 75 | | | 90 | 95 |
| | | | | | | | | (0) | | | | (5) | |
| 2 | 4.48 | 3 | 0.28 | | | | | 95 | 85 | | | 100 | 95 |
| | | | | | | | | (0) | | | | (0) | |
| 2 | 6.72 | 4 | 0.28 | | | | | 100 | 90 | | | 100 | 95 |
| | | | | | | | | (0) | | | | (0) | |
| 2 | 6.72 | 5 | 0.28 | | | | | 60 | 70 | | | 100 | 85 |
| | | | | | | | | (14) | | | | (0) | |
| 2 | 6.72 | 6 | 0.28 | | | | | | | | | 100 | 85 |

TABLE II-continued

| HERBICIDE | | ANTIDOTE | | SORGHUM | | WHEAT | | RICE | | SOYBEAN | | CORN | |
|---|---|---|---|---|---|---|---|---|---|---|---|---|---|
| No. | RATE | No. | RATE | W | WO | W | WO | W | WO | W | WO | W | WO |
| 2 | 6.72 | 7 | 0.28 | | | | | | | 100 | 85 (0) | | |
| 2 | 6.72 | 8 | 0.28 | | | | | | | 95 | 85 (0) | | |
| 2 | 4.48 | 9 | 0.28 | | | | | | | 90 | 95 (0) | | |
| 2 | 4.48 | 10 | 0.28 | | | | | | | 95 | 100 (5) | | |
| 2 | 4.48 | 11 | 0.28 | | | | | | | 100 | 100 (5) | | |
| 2 | 4.48 | 12 | 0.28 | | | | | | | 90 | 95 (0) | | |
| 2 | 4.48 | 13 | 0.28 | | | | | | | 100 | 100 (5) | | |
| 2 | 4.48 | 14 | 0.28 | | | | | | | 100 | 100 (0) | | |
| 2 | 4.48 | 15 | 0.28 | | | | | | | 100 | 95 (0) | | |
| 2 | 4.48 | 16 | 0.28 | | | | | | | 95 | 100 (5) | | |
| 2 | 4.48 | 17 | 0.28 | | | | | | | 100 | 100 (0) | | |
| 2 | 4.48 | 18 | 0.28 | | | | | | | 85 | 100 (15) | | |
| 3 | 2.24 | 1 | 0.28 | 30 | 100 (70) | 70 | 90 (22) | | | | | | |
| 3 | 2.24 | 2 | 0.28 | 100 | 100 (0) | 95 | 95 (0) | | | | | | |
| 3 | 2.24 | 3 | 0.28 | 100 | 100 (0) | 100 | 95 (0) | | | | | | |
| 3 | 2.24 | 4 | 0.28 | 60 | 100 (40) | 50 | 90 (44) | | | | | | |
| 3 | 2.24 | 5 | 0.28 | 85 | 100 (15) | 30 | 70 (57) | | | | | | |
| 3 | 2.24 | 6 | 0.28 | 95 | 100 (5) | 80 | 90 (11) | | | | | | |
| 3 | 2.24 | 7 | 0.28 | 60 | 100 (40) | 60 | 90 (33) | | | | | | |
| 3 | 2.24 | 8 | 0.28 | 50 | 100 (50) | 50 | 95 (47) | | | | | | |
| 3 | 2.24 | 9 | 0.28 | 45 | 100 (55) | 35 | 80 (56) | | | | | | |
| 3 | 2.24 | 10 | 0.28 | 60 | 100 (40) | 60 | 95 (36) | | | | | | |
| 3 | 2.24 | 11 | 0.28 | 100 | 100 (0) | 70 | 100 (30) | | | | | | |
| 3 | 2.24 | 12 | 0.28 | 35 | 100 (65) | 45 | 90 (50) | | | | | | |
| 3 | 2.24 | 13 | 0.28 | 100 | 100 (0) | 95 | 100 (5) | | | | | | |
| 3 | 2.24 | 14 | 0.28 | 95 | 100 (5) | 95 | 90 (0) | | | | | | |
| 3 | 2.24 | 15 | 0.28 | 100 | 100 (0) | 75 | 100 (25) | | | | | | |
| 3 | 2.24 | 16 | 0.28 | 100 | 100 (0) | 95 | 100 (5) | | | | | | |
| 3 | 2.24 | 17 | 0.28 | 100 | 100 (0) | 90 | 100 (10) | | | | | | |
| 3 | 2.24 | 18 | 0.28 | 95 | 100 (5) | 95 | 100 (5) | | | | | | |
| 3 | 2.24 | 19 | 0.28 | 100 | 100 (0) | 80 | 80 (0) | | | | | | |
| 3 | 2.24 | 21 | 0.28 | 90 | 95 (5) | | | | | | | | |
| 4 | 4.48 | 1 | 0.28 | | | | | 45 | 95 (52) | | | | |
| 4 | 4.48 | 2 | 0.28 | | | | | 100 | 95 (0) | | | | |
| 4 | 4.48 | 3 | 0.28 | | | | | 85 | 95 (10) | | | | |
| 4 | 4.48 | 4 | 0.28 | | | | | 70 | 95 (26) | | | | |
| 4 | 4.48 | 5 | 0.28 | | | | | 55 | 95 (42) | | | | |
| 4 | 4.48 | 6 | 0.28 | | | | | 95 | 90 (0) | | | | |
| 4 | 4.48 | 7 | 0.28 | | | | | 90 | 90 | | | | |

TABLE II-continued

| HERBICIDE | | ANTIDOTE | | % PLANT INHIBITION AND % SAFENING EFFECT ( ) | | | | | | | | | |
|---|---|---|---|---|---|---|---|---|---|---|---|---|---|
| | | | | SORGHUM | | WHEAT | | RICE | | SOYBEAN | | CORN | |
| No. | RATE | No. | RATE | W | WO | W | WO | W | WO | W | WO | W | WO |
| 4 | 4.48 | 8 | 0.28 | | | | | 90 (0) | 90 | | | | |
| 4 | 4.48 | 9 | 0.28 | | | | | 75 (0) | 80 | | | | |
| 4 | 4.48 | 10 | 0.28 | | | | | 95 (6) | 60 | | | | |
| 4 | 4.48 | 11 | 0.28 | | | | | 100 (0) | 100 | | | | |
| 4 | 4.48 | 12 | 0.28 | | | | | 65 (0) | 95 | | | | |
| 4 | 4.48 | 13 | 0.28 | | | | | 100 (31) | 100 | | | | |
| 4 | 4.48 | 14 | 0.28 | | | | | 95 (0) | 95 | | | | |
| 4 | 4.48 | 15 | 0.28 | | | | | 100 (0) | 100 | | | | |
| 4 | 4.48 | 16 | 0.28 | | | | | 95 (0) | 95 | | | | |
| 4 | 4.48 | 17 | 0.28 | | | | | 80 (0) | 95 | | | | |
| 4 | 4.48 | 18 | 0.28 | | | | | 75 (15) | 95 | | | | |
| 4 | 4.48 | 19 | 0.28 | | | | | 95 (21) | 95 | | | | |
| 6 | 2.24 | 1 | 0.28 | | | | | | (0) | 60 | 50 | 0 (100) | 90 |
| 6 | 2.24 | 2 | 0.28 | | | | | | | 80 (0) | 70 | 95 (0) | 95 |
| 6 | 2.24 | 3 | 0.28 | | | | | | | 60 (7) | 65 | 95 (0) | 95 |
| 6 | 2.24 | 4 | 0.28 | | | | | | | 90 (0) | 70 | 30 (68) | 95 |
| 6 | 2.24 | 5 | 0.28 | | | | | | | 90 (0) | 85 | 50 (47) | 95 |
| 6 | 2.24 | 6 | 0.28 | | | | | | | 70 (0) | 70 | 95 (0) | 95 |
| 6 | 2.24 | 7 | 0.28 | | | | | | | 80 (0) | 70 | 95 (0) | 95 |
| 6 | 2.24 | 8 | 0.28 | | | | | | | 80 (0) | 70 | 40 (55) | 90 |
| 6 | 2.24 | 9 | 0.28 | | | | | | | 85 (0) | 40 | 65 (31) | 95 |
| 6 | 2.24 | 10 | 0.28 | | | | | | | 15 (70) | 50 | 30 (70) | 100 |
| 6 | 2.24 | 11 | 0.28 | | | | | | | 65 (0) | 65 | 95 (0) | 90 |
| 6 | 2.24 | 12 | 0.28 | | | | | | | 60 (0) | 50 | 15 (85) | 100 |
| 6 | 2.24 | 13 | 0.28 | | | | | | | 90 (0) | 70 | 90 (5) | 95 |
| 6 | 2.24 | 14 | 0.28 | | | | | | | 30 (50) | 60 | 95 (5) | 100 |
| 6 | 2.24 | 15 | 0.28 | | | | | | | 90 (0) | 75 | 100 (0) | 100 |
| 6 | 2.24 | 16 | 0.28 | | | | | | | 75 (11) | 85 | 100 (0) | 100 |
| 6 | 2.24 | 17 | 0.28 | | | | | | | 95 (0) | 75 | 60 (40) | 100 |
| 6 | 2.24 | 18 | 0.28 | | | | | | | 100 (0) | 75 | 35 (65) | 100 |
| 6 | 2.24 | 19 | 0.28 | | | | | | | 80 (5) | 85 | 100 (0) | 90 |

EXAMPLE 24

The following procedure shows interaction between herbicide and antidote when both are incorporated in a soil cover layer before emergence of crop and weed species. Containers were filled and compacted with a fumigated silt loam soil to a depth of about 1.3 cm from the top of the container. A first container was designated as an untreated control, a second container was designated as a herbicide control, and a third container was designated as a herbicide+antidote test container. Each of the containers was seeded with both crop and weed species. A measured amount of herbicide dispersed or dissolved in acetone was applied to a measured quantity of soil. To this same quantity of soil treated with herbicide there was added a measured amount of antidote dispersed or dissolved in acetone. The quantity of soil of treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a greenhouse bench and sub-irrigated as required for the duration of the test. Plant response was observed about three weeks after initial treatment. Results are reported in Table III.

TABLE III

| HERBICIDE | | ANTIDOTE | | % PLANT INHIBITION AND % SAFENING EFFECT ( ) | | | | | | | | | | | | | |
|---|---|---|---|---|---|---|---|---|---|---|---|---|---|---|---|---|---|
| | | | | BARNYARD GRASS | | RICE | | WHEAT | | GREEN FOXTAIL | | CORN | | WILD OATS | | SORGHUM | |
| No. | RATE | No. | RATE | W | WO | W | WO | W | WO | W | WO | W | WO | W | WO | W | WO |
| 1 | 0.14 | 9 | 2.24 | | | | | 85 | 65 (0) | | | | | 95 | 100 (5) | | |
| 1 | 0.14 | 9 | 8.96 | | | | | 40 | 65 (38) | | | | | 85 | 100 (15) | | |
| 1 | 0.56 | 9 | 2.24 | | | | | 85 | 100 (15) | | | | | 100 | 100 (0) | | |
| 1 | 0.56 | 9 | 8.96 | | | | | 95 | 100 (5) | | | | | 100 | 100 (0) | | |
| 1 | 0.14 | 15 | 2.24 | | | | | 30 | 20 (0) | | | | | 95 | 95 (0) | | |
| 1 | 0.14 | 15 | 8.96 | | | | | 40 | 20 (0) | | | | | 75 | 95 (21) | | |
| 1 | 0.56 | 15 | 2.24 | | | | | 70 | 70 (0) | | | | | 100 | 100 (0) | | |
| 1 | 0.56 | 15 | 8.96 | | | | | 55 | 70 (21) | | | | | 100 | 100 (0) | | |
| 1 | 0.14 | 16 | 2.24 | | | | | 35 | 20 (0) | | | | | 95 | 95 (0) | | |
| 1 | 0.14 | 16 | 8.96 | | | | | 10 | 20 (50) | | | | | 75 | 95 (21) | | |
| 1 | 0.56 | 16 | 2.24 | | | | | 80 | 85 (5) | | | | | 100 | 100 (0) | | |
| 1 | 0.56 | 16 | 8.96 | | | | | 35 | 85 (58) | | | | | 100 | 100 (0) | | |
| 3 | 0.56 | 1 | 2.24 | | | | | 60 | 65 (7) | 100 | 100 (0) | | | | | 100 | 100 (0) |
| 3 | 0.56 | 1 | 8.96 | | | | | 25 | 65 (61) | 100 | 100 (0) | | | | | 80 | 100 (20) |
| 3 | 2.24 | 1 | 2.24 | | | | | 85 | 90 (5) | 100 | 100 (0) | | | | | 100 | 100 (0) |
| 3 | 2.24 | 1 | 8.96 | | | | | 85 | 90 (5) | 100 | 100 (0) | | | | | 95 | 100 (5) |
| 3 | 0.56 | 4 | 2.24 | | | | | | | 100 | 100 (0) | | | | | 80 | 100 (20) |
| 3 | 0.56 | 4 | 2.24 | | | | | 90 | 80 (0) | 100 | 100 (0) | | | | | | |
| 3 | 0.56 | 4 | 8.96 | | | | | 35 | 80 (56) | 100 | 100 (0) | | | | | | |
| 3 | 0.56 | 4 | 8.96 | | | | | | | 100 | 100 (0) | | | | | 85 | 100 (15) |
| 3 | 2.24 | 4 | 2.24 | | | | | | | 100 | 100 (0) | | | | | 100 | 100 (0) |
| 3 | 2.24 | 4 | 2.24 | | | | | 95 | 95 (0) | 100 | 100 (0) | | | | | | |
| 3 | 2.24 | 4 | 8.96 | | | | | 95 | 95 (0) | 100 | 100 (0) | | | | | | |
| 3 | 2.24 | 4 | 8.96 | | | | | | | 100 | 100 (0) | | | | | 65 | 100 (35) |
| 3 | 0.56 | 5 | 2.24 | | | | | 30 | 75 (60) | 100 | 100 (0) | | | | | | |
| 3 | 0.56 | 5 | 8.96 | | | | | 10 | 75 (86) | 100 | 100 (0) | | | | | | |
| 3 | 2.24 | 5 | 2.24 | | | | | 95 | 90 (0) | 100 | 100 (0) | | | | | | |
| 3 | 2.24 | 5 | 8.96 | | | | | 65 | 90 (27) | 100 | 100 (0) | | | | | | |
| 3 | 0.56 | 7 | 2.24 | | | | | | | 100 | 100 (0) | | | | | 80 | 90 (11) |
| 3 | 0.56 | 7 | 8.96 | | | | | | | 100 | 100 (0) | | | | | 55 | 90 (38) |
| 3 | 2.24 | 7 | 2.24 | | | | | | | 100 | 100 (0) | | | | | 100 | 100 (0) |
| 3 | 2.24 | 7 | 8.96 | | | | | | | 100 | 100 (0) | | | | | 100 | 100 (0) |
| 3 | 0.56 | 8 | 2.24 | | | | | | | 100 | 100 (0) | | | | | 45 | 90 (50) |
| 3 | 0.56 | 8 | 2.24 | | | | | 25 | 25 (0) | 100 | 100 (0) | | | | | | |
| 3 | 0.56 | 8 | 8.96 | | | | | | | 100 | 100 (0) | | | | | 20 | 90 (77) |
| 3 | 0.56 | 8 | 8.96 | | | | | 35 | 25 | 100 | 100 | | | | | | |

TABLE III-continued

| | | | | % PLANT INHIBITION AND % SAFENING EFFECT ( ) | | | | | | | | | | | |
|---|---|---|---|---|---|---|---|---|---|---|---|---|---|---|---|
| HERBICIDE | | ANTIDOTE | | BARNYARD GRASS | | RICE | | WHEAT | | GREEN FOXTAIL | | CORN | | WILD OATS | | SORGHUM | |
| No. | RATE | No. | RATE | W | WO | W | WO | W | WO | W | WO | W | WO | W | WO | W | WO |
| 3 | 2.24 | 8 | 2.24 | | | | | | (0) | 100 | 100 | | | | | 70 | 95 (26) |
| 3 | 2.24 | 8 | 2.24 | | | | | 75 | 60 (0) | 100 | 100 (0) | | | | | | |
| 3 | 2.24 | 8 | 8.96 | | | | | 60 | 60 (0) | 100 | 100 (0) | | | | | | |
| 3 | 2.24 | 8 | 8.96 | | | | | | | 100 | 100 (0) | | | | | 50 | 95 (47) |
| 3 | 0.56 | 9 | 2.24 | | | | | 60 | 75 (20) | 100 | 100 (0) | | | | | | |
| 3 | 0.56 | 9 | 2.24 | | | | | | | 100 | 100 (0) | | | | | 65 | 95 (31) |
| 3 | 0.56 | 9 | 8.96 | | | | | | | 100 | 100 (0) | | | | | 60 | 95 (36) |
| 3 | 0.56 | 9 | 8.96 | | | | | 10 | 75 (86) | 100 | 100 (0) | | | | | | |
| 3 | 2.24 | 9 | 2.24 | | | | | | | 100 | 100 (0) | | | | | 100 | 95 (0) |
| 3 | 2.24 | 9 | 2.24 | | | | | 85 | 80 (0) | 100 | 100 (0) | | | | | | |
| 3 | 2.24 | 9 | 8.96 | | | | | | | 100 | 100 (0) | | | | | 90 | 95 (5) |
| 3 | 2.24 | 9 | 8.96 | | | | | 35 | 80 (56) | 100 | 100 (0) | | | | | | |
| 3 | 0.56 | 10 | 2.24 | | | | | | | 100 | 100 (0) | | | | | 75 | 100 (25) |
| 3 | 0.56 | 10 | 8.96 | | | | | | | 100 | 100 (0) | | | | | 70 | 100 (30) |
| 3 | 2.24 | 10 | 2.24 | | | | | | | 100 | 100 (0) | | | | | 95 | 100 (5) |
| 3 | 2.24 | 10 | 8.96 | | | | | | | 100 | 100 (0) | | | | | 75 | 100 (25) |
| 3 | 0.56 | 12 | 2.24 | | | | | | | 100 | 100 (0) | | | | | 40 | 95 (57) |
| 3 | 0.56 | 12 | 8.96 | | | | | | | 100 | 100 (0) | | | | | 25 | 95 (73) |
| 3 | 1.12 | 12 | 2.24 | | | | | 40 | 80 (50) | 100 | 100 (0) | | | | | | |
| 3 | 1.12 | 12 | 8.96 | | | | | 5 | 80 (93) | 100 | 100 (0) | | | | | | |
| 3 | 2.24 | 12 | 2.24 | | | | | | | 100 | 100 (0) | | | | | 60 (40) | 100 |
| 3 | 2.24 | 12 | 8.96 | | | | | | | 100 | 100 (0) | | | | | 70 (30) | 100 |
| 3 | 4.48 | 12 | 2.24 | | | | | 80 | 85 (5) | 100 | 100 (0) | | | | | | |
| 3 | 4.48 | 12 | 8.96 | | | | | 65 | 85 (23) | 100 | 100 (0) | | | | | | |
| 4 | 1.12 | 1 | 2.24 | 100 | 100 (0) | 55 | 45 (0) | | | | | | | | | | |
| 4 | 1.12 | 1 | 8.96 | 100 | 100 (0) | 50 | 45 (0) | | | | | | | | | | |
| 4 | 4.48 | 1 | 2.24 | 100 | 100 (0) | 55 | 95 (42) | | | | | | | | | | |
| 4 | 4.48 | 1 | 8.96 | 100 | 100 (0) | 20 | 95 (78) | | | | | | | | | | |
| 4 | 1.12 | 5 | 2.24 | 90 | 100 (10) | 30 | 60 (50) | | | | | | | | | | |
| 4 | 1.12 | 5 | 8.96 | 95 | 100 (5) | 55 | 60 (8) | | | | | | | | | | |
| 4 | 4.48 | 5 | 2.24 | 100 | 100 (0) | 75 | 80 (6) | | | | | | | | | | |
| 4 | 4.48 | 5 | 8.96 | 100 | 100 (0) | 60 | 80 (25) | | | | | | | | | | |
| 6 | 0.56 | 1 | 0.56 | 100 | 100 (0) | | | | | | | 5 | 80 (93) | | | | |
| 6 | 0.56 | 1 | 2.24 | 100 | 100 (0) | | | | | | | 10 | 80 (87) | | | | |
| 6 | 0.56 | 1 | 2.24 | 100 | 100 (0) | | | | | 100 | 100 (0) | 15 | 90 (83) | | | | |
| 6 | 0.56 | 1 | 8.96 | 100 | 100 (0) | | | | | | | 5 | 80 (93) | | | | |
| 6 | 0.56 | 1 | 8.96 | 100 | 100 (0) | | | | | 100 | 100 (0) | 30 | 90 (66) | | | | |
| 6 | 2.24 | 1 | 0.56 | 100 | 100 (0) | | | | | | | 75 | 95 (21) | | | | |

TABLE III-continued

| | | | | % PLANT INHIBITION AND % SAFENING EFFECT ( ) | | | | | | | | | | | | |
|---|---|---|---|---|---|---|---|---|---|---|---|---|---|---|---|---|
| HERBICIDE | | ANTIDOTE | | BARNYARD GRASS | | RICE | | WHEAT | | GREEN FOXTAIL | | CORN | | WILD OATS | | SORGHUM | |
| No. | RATE | No. | RATE | W | WO | W | WO | W | WO | W | WO | W | WO | W | WO | W | WO |
| 6 | 2.24 | 1 | 2.24 | 100 | 100 (0) | | | | | 100 | 100 (0) | 25 | 95 (73) | | | | |
| 6 | 2.24 | 1 | 2.24 | 100 | 100 (0) | | | | | | | 60 | 95 (36) | | | | |
| 6 | 2.24 | 1 | 8.96 | 100 | 100 (0) | | | | | 100 | 100 (0) | 15 | 95 (84) | | | | |
| 6 | 2.24 | 1 | 8.96 | 100 | 100 (0) | | | | | | | 5 | 95 (94) | | | | |
| 6 | 0.56 | 4 | 2.24 | 100 | 100 (0) | | | | | 100 | 100 (0) | 10 | 80 (87) | | | | |
| 6 | 0.56 | 4 | 8.96 | 100 | 100 (0) | | | | | 100 | 100 (0) | 40 | 80 (50) | | | | |
| 6 | 2.24 | 4 | 2.24 | 100 | 100 (0) | | | | | 100 | 100 (0) | 65 | 95 (31) | | | | |
| 6 | 2.24 | 4 | 8.96 | 100 | 100 (0) | | | | | 100 | 100 (0) | 60 | 95 (36) | | | | |
| 6 | 0.56 | 5 | 2.24 | 100 | 100 (0) | | | | | | | 10 | 85 (88) | | | | |
| 6 | 0.56 | 5 | 8.96 | 100 | 100 (0) | | | | | | | 5 | 85 (94) | | | | |
| 6 | 2.24 | 5 | 2.24 | 100 | 100 (0) | | | | | | | 25 | 95 (73) | | | | |
| 6 | 2.24 | 5 | 8.96 | 100 | 100 (0) | | | | | | | 20 | 95 (78) | | | | |
| 6 | 0.56 | 8 | 2.24 | 100 | 100 (0) | | | | | | | 20 | 25 (20) | | | | |
| 6 | 0.56 | 8 | 8.96 | 100 | 100 (0) | | | | | | | 5 | 25 (80) | | | | |
| 6 | 2.24 | 8 | 2.24 | 100 | 100 (0) | | | | | | | 5 | 95 (94) | | | | |
| 6 | 2.24 | 8 | 8.96 | 100 | 100 (0) | | | | | | | 5 | 95 (94) | | | | |
| 6 | 0.56 | 10 | 2.24 | 100 | 100 (0) | | | | | | | 15 | 95 (84) | | | | |
| 6 | 0.56 | 10 | 8.96 | 100 | 100 (0) | | | | | | | 15 | 95 (84) | | | | |
| 6 | 2.24 | 10 | 2.24 | 100 | 100 (0) | | | | | | | 30 | 95 (68) | | | | |
| 6 | 2.24 | 10 | 8.96 | 100 | 100 (0) | | | | | | | 30 | 95 (68) | | | | |
| 6 | 0.56 | 11 | 0.56 | 100 | 100 (0) | | | | | | | 35 | 90 (61) | | | | |
| 6 | 0.56 | 11 | 2.24 | 100 | 100 (0) | | | | | | | 20 | 90 (77) | | | | |
| 6 | 0.56 | 11 | 8.96 | 100 | 100 (0) | | | | | | | 10 | 90 (88) | | | | |
| 6 | 2.24 | 11 | 0.56 | 100 | 100 (0) | | | | | | | 85 | 95 (10) | | | | |
| 6 | 2.24 | 11 | 2.24 | 100 | 100 (0) | | | | | | | 65 | 95 (31) | | | | |
| 6 | 2.24 | 11 | 8.96 | 100 | 100 (0) | | | | | | | 30 | 95 (68) | | | | |
| 6 | 0.56 | 12 | 2.24 | 100 | 100 (0) | | | | | | | 5 | 95 (94) | | | | |
| 6 | 0.56 | 12 | 8.96 | 100 | 100 (0) | | | | | | | 0 | 95 (100) | | | | |
| 6 | 2.24 | 12 | 2.24 | 100 | 100 (0) | | | | | | | 5 | 100 (95) | | | | |
| 6 | 2.24 | 12 | 8.96 | 100 | 100 (0) | | | | | | | 5 | 100 (95) | | | | |
| 6 | 0.56 | 17 | 0.56 | 100 | 100 (0) | | | | | | | 0 | 10 (100) | | | | |
| 6 | 0.56 | 17 | 0.56 | 90 | 95 (5) | | | | | | | 5 | 35 (85) | | | | |
| 6 | 0.56 | 17 | 2.24 | 100 | 100 (0) | | | | | | | 5 | 10 (50) | | | | |
| 6 | 0.56 | 17 | 2.24 | 95 | 95 (0) | | | | | | | 0 | 35 (100) | | | | |
| 6 | 0.56 | 17 | 8.96 | 100 | 100 (0) | | | | | | | 5 | 10 (50) | | | | |
| 6 | 0.56 | 17 | 8.96 | 90 | 95 (5) | | | | | | | 0 | 35 (100) | | | | |
| 6 | 2.24 | 17 | 0.56 | 95 | 100 (5) | | | | | | | 10 | 65 (84) | | | | |
| 6 | 2.24 | 17 | 0.56 | 100 | 100 (0) | | | | | | | 10 | 45 (77) | | | | |
| 6 | 2.24 | 17 | 2.24 | 100 | 100 | | | | | | | 5 | 45 | | | | |

TABLE III-continued

| HERBICIDE | | ANTIDOTE | | BARNYARD GRASS | | RICE | | WHEAT | | GREEN FOXTAIL | | CORN | | WILD OATS | | SORGHUM | |
|---|---|---|---|---|---|---|---|---|---|---|---|---|---|---|---|---|---|
| No. | RATE | No. | RATE | W | WO | W | WO | W | WO | W | WO | W | WO | W | WO | W | WO |
| 6 | 2.24 | 17 | 2.24 | 95 | 100 | | | | | | | 5 | 65 | | | | |
| | | | | (0) | | | | | | | | (88) | | | | | |
| 6 | 2.24 | 17 | 8.96 | 95 | 100 | | | | | | | 15 | 65 | | | | |
| | | | | (5) | | | | | | | | (92) | | | | | |
| 6 | 2.24 | 17 | 8.96 | 100 | 100 | | | | | | | 5 | 45 | | | | |
| | | | | (5) | | | | | | | | (76) | | | | | |
| 6 | 0.56 | 18 | 0.56 | 95 | 95 | | | | | | | 10 | 30 | | | | |
| | | | | (0) | | | | | | | | (88) | | | | | |
| 6 | 0.56 | 18 | 2.24 | 95 | 95 | | | | | | | 0 | 30 | | | | |
| | | | | (0) | | | | | | | | (66) | | | | | |
| 6 | 0.56 | 18 | 8.96 | 95 | 95 | | | | | | | 0 | 30 | | | | |
| | | | | (0) | | | | | | | | (100) | | | | | |
| 6 | 2.24 | 18 | 0.56 | 95 | 95 | | | | | | | 10 | 50 | | | | |
| | | | | (0) | | | | | | | | (80) | | | | | |
| 6 | 2.24 | 18 | 2.24 | 100 | 95 | | | | | | | 5 | 50 | | | | |
| | | | | (0) | | | | | | | | (90) | | | | | |
| 6 | 2.24 | 18 | 8.96 | 100 | 95 | | | | | | | 10 | 50 | | | | |
| | | | | (0) | | | | | | | | (80) | | | | | |
| 6 | 0.56 | 20 | 0.56 | 100 | 95 | | | | | | | 10 | 25 | | | | |
| | | | | (0) | | | | | | | | (60) | | | | | |
| 6 | 0.56 | 20 | 2.24 | 100 | 95 | | | | | | | 0 | 25 | | | | |
| | | | | (0) | | | | | | | | (100) | | | | | |
| 6 | 0.56 | 20 | 8.96 | 100 | 95 | | | | | | | 10 | 25 | | | | |
| | | | | (0) | | | | | | | | (60) | | | | | |
| 6 | 2.24 | 20 | 0.56 | 100 | 100 | | | | | | | 10 | 90 | | | | |
| | | | | (0) | | | | | | | | (88) | | | | | |
| 6 | 2.24 | 20 | 2.24 | 95 | 100 | | | | | | | 15 | 90 | | | | |
| | | | | (5) | | | | | | | | (83) | | | | | |
| 6 | 2.24 | 20 | 8.96 | 100 | 100 | | | | | | | 15 | 90 | | | | |
| | | | | (0) | | | | | | | | (83) | | | | | |
| 6 | 0.56 | 21 | 0.56 | 100 | 95 | | | | | | | 5 | 25 | | | | |
| | | | | (0) | | | | | | | | (80) | | | | | |
| 6 | 0.56 | 21 | 2.24 | 100 | 95 | | | | | | | 0 | 25 | | | | |
| | | | | (0) | | | | | | | | (100) | | | | | |
| 6 | 0.56 | 21 | 8.96 | 100 | 95 | | | | | | | 5 | 25 | | | | |
| | | | | (0) | | | | | | | | (80) | | | | | |
| 6 | 2.24 | 21 | 0.56 | 100 | 100 | | | | | | | 55 | 90 | | | | |
| | | | | (0) | | | | | | | | (38) | | | | | |
| 6 | 2.24 | 21 | 2.24 | 95 | 100 | | | | | | | 5 | 90 | | | | |
| | | | | (5) | | | | | | | | (94) | | | | | |
| 6 | 2.24 | 21 | 8.96 | 100 | 100 | | | | | | | 5 | 90 | | | | |
| | | | | (0) | | | | | | | | (94) | | | | | |

EXAMPLE 25

The following procedure shows interaction between a herbicide and antidote when applied together as a mixture before emergence of the crop and weed species. Containers were filled and compacted with fumigated silt loam soil to a depth of about 1.3 cm from the top of the container. A first container was designated as an untreated control, a second container was designated as a herbicide control, and a third container was designated as a herbicide+antidote test container. Each of the containers was seeded with both crop plant and weed species. The herbicide+antidote mixture was applied to the seeded containers either by a procedure of topical application of the mixture to a soil layer placed over the seed bed followed by watering to achieve incorporation, or by a procedure of incorporation of a quantity of the mixture into soil and then placement of the treated soil into the container over the seed bed. The containers were then placed on a greenhouse bench and sub-irrigated as required for the duration of the test. Plant response was observed about three weeks after initial treatment. Results are reported in Table IV.

TABLE IV

| HERBICIDE | | ANTIDOTE | | CORN | | GREEN FOXTAIL | | BARNYARD GRASS | | CRAB GRASS | |
|---|---|---|---|---|---|---|---|---|---|---|---|
| No. | RATE | No. | RATE | W | WO | W | WO | W | WO | W | WO |
| 5 | 4.48 | 1 | 0.14 | 0 | 55 | 100 | 100 | 100 | 100 | | |
| | | | | (100) | | (0) | | (0) | | | |
| 5 | 4.48 | 1 | 0.14 | 5 | 68 | 100 | 100 | 100 | 100 | | |
| | | | | (92) | | (0) | | (0) | | | |
| 5 | 4.48 | 1 | 0.14 | 35 | 73 | 100 | 100 | 100 | 100 | | |
| | | | | (52) | | (0) | | (0) | | | |
| 5 | 4.48 | 1 | 0.14 | 0 | 20 | 100 | 100 | 100 | 98 | | |
| | | | | (100) | | (0) | | (0) | | | |
| 5 | 4.48 | 1 | 0.14 | 20 | 88 | 100 | 100 | 100 | 100 | | |
| | | | | (77) | | (0) | | (0) | | | |

TABLE IV-continued

% PLANT INHIBITION AND % SAFENING EFFECT ( )

| HERBICIDE | | ANTIDOTE | | CORN | | GREEN FOXTAIL | | BARNYARD GRASS | | CRAB GRASS | |
|---|---|---|---|---|---|---|---|---|---|---|---|
| No. | RATE | No. | RATE | W | WO | W | WO | W | WO | W | WO |
| 5 | 4.48 | 1 | 0.14 | 70 | 75 | 100 | 100 | 100 | 100 | | |
| | | | | (6) | | (0) | | (0) | | | |
| 5 | 4.48 | 1 | 0.56 | 0 | 55 | 100 | 100 | 100 | 100 | | |
| | | | | (100) | | (0) | | (0) | | | |
| 5 | 4.48 | 1 | 0.56 | 10 | 73 | 100 | 100 | 100 | 100 | | |
| | | | | (86) | | (0) | | (0) | | | |
| 5 | 4.48 | 1 | 0.56 | 10 | 68 | 100 | 100 | 100 | 100 | | |
| | | | | (85) | | (0) | | (0) | | | |
| 5 | 4.48 | 1 | 0.56 | 0 | 20 | 100 | 100 | 100 | 98 | | |
| | | | | (100) | | (0) | | (0) | | | |
| 5 | 4.48 | 1 | 0.56 | 70 | 75 | 100 | 100 | 100 | 100 | | |
| | | | | (6) | | (0) | | (0) | | | |
| 5 | 4.48 | 1 | 0.56 | 10 | 88 | 100 | 100 | 100 | 100 | | |
| | | | | (88) | | (0) | | (0) | | | |
| 5 | 4.48 | 1 | 2.24 | 0 | 55 | 100 | 100 | 100 | 100 | | |
| | | | | (100) | | (0) | | (0) | | | |
| 5 | 4.48 | 1 | 2.24 | 38 | 75 | 100 | 100 | 100 | 100 | | |
| | | | | (49) | | (0) | | (0) | | | |
| 5 | 4.48 | 1 | 2.24 | 5 | 73 | 100 | 100 | 100 | 100 | | |
| | | | | (93) | | (0) | | (0) | | | |
| 5 | 4.48 | 1 | 2.24 | 8 | 88 | 100 | 100 | 100 | 100 | | |
| | | | | (90) | | (0) | | (0) | | | |
| 5 | 4.48 | 1 | 2.24 | 0 | 68 | 100 | 100 | 100 | 100 | | |
| | | | | (100) | | (0) | | (0) | | | |
| 5 | 4.48 | 1 | 2.24 | 0 | 20 | 100 | 100 | 100 | 98 | | |
| | | | | (100) | | (0) | | (0) | | | |
| 5 | 6.72 | 1 | 0.14 | 50 | 92 | 100 | 100 | 100 | 100 | | |
| | | | | (45) | | (0) | | (0) | | | |
| 5 | 6.72 | 1 | 0.14 | 23 | 55 | 100 | 100 | 100 | 100 | | |
| | | | | (58) | | (0) | | (0) | | | |
| 5 | 6.72 | 1 | 0.14 | 20 | 95 | 100 | 100 | 100 | 100 | | |
| | | | | (78) | | (0) | | (0) | | | |
| 5 | 6.72 | 1 | 0.14 | 18 | 62 | 100 | 100 | 100 | 100 | | |
| | | | | (70) | | (0) | | (0) | | | |
| 5 | 6.72 | 1 | 0.14 | 13 | 78 | 100 | 100 | 100 | 100 | | |
| | | | | (83) | | (0) | | (0) | | | |
| 5 | 6.72 | 1 | 0.14 | 65 | 83 | 100 | 100 | 100 | 100 | | |
| | | | | (21) | | (0) | | (0) | | | |
| 5 | 6.72 | 1 | 0.56 | 10 | 62 | 100 | 100 | 100 | 100 | | |
| | | | | (83) | | (0) | | (0) | | | |
| 5 | 6.72 | 1 | 0.56 | 5 | 55 | 100 | 100 | 100 | 100 | | |
| | | | | (90) | | (0) | | (0) | | | |
| 5 | 6.72 | 1 | 0.56 | 20 | 92 | 100 | 100 | 100 | 100 | | |
| | | | | (78) | | (0) | | (0) | | | |
| 5 | 6.72 | 1 | 0.56 | 13 | 95 | 100 | 100 | 100 | 100 | | |
| | | | | (86) | | (0) | | (0) | | | |
| 5 | 6.72 | 1 | 0.56 | 68 | 83 | 100 | 100 | 100 | 100 | | |
| | | | | (18) | | (0) | | (0) | | | |
| 5 | 6.72 | 1 | 0.56 | 8 | 78 | 100 | 100 | 100 | 100 | | |
| | | | | (89) | | (0) | | (0) | | | |
| 5 | 6.72 | 1 | 2.24 | 0 | 55 | 100 | 100 | 100 | 100 | | |
| | | | | (100) | | (0) | | (0) | | | |
| 5 | 6.72 | 1 | 2.24 | 70 | 83 | 100 | 100 | 100 | 100 | | |
| | | | | (15) | | (0) | | (0) | | | |
| 5 | 6.72 | 1 | 2.24 | 5 | 92 | 100 | 100 | 100 | 100 | | |
| | | | | (94) | | (0) | | (0) | | | |
| 5 | 6.72 | 1 | 2.24 | 10 | 62 | 100 | 100 | 100 | 100 | | |
| | | | | (83) | | (0) | | (0) | | | |
| 5 | 6.72 | 1 | 2.24 | 0 | 78 | 100 | 100 | 100 | 100 | | |
| | | | | (100) | | (0) | | (0) | | | |
| 5 | 6.72 | 1 | 2.24 | 5 | 95 | 100 | 100 | 100 | 100 | | |
| | | | | (94) | | (0) | | (0) | | | |
| 5 | 8.96 | 1 | 0.14 | 58 | 95 | 100 | 100 | 100 | 100 | | |
| | | | | (38) | | (0) | | (0) | | | |
| 5 | 8.96 | 1 | 0.14 | 33 | 95 | 100 | 100 | 100 | 100 | | |
| | | | | (65) | | (0) | | (0) | | | |
| 5 | 8.96 | 1 | 0.14 | 5 | 45 | 100 | 100 | 100 | 100 | | |
| | | | | (88) | | (0) | | (0) | | | |
| 5 | 8.96 | 1 | 0.14 | 33 | 92 | 100 | 100 | 100 | 100 | | |
| | | | | (64) | | (0) | | (0) | | | |
| 5 | 8.96 | 1 | 0.14 | 73 | 85 | 100 | 100 | 100 | 100 | | |
| | | | | (14) | | (0) | | (0) | | | |
| 5 | 8.96 | 1 | 0.14 | 25 | 78 | 100 | 100 | 100 | 100 | | |
| | | | | (67) | | (0) | | (0) | | | |
| 5 | 8.96 | 1 | 0.56 | 25 | 92 | 100 | 100 | 100 | 100 | | |
| | | | | (72) | | (0) | | (0) | | | |
| 5 | 8.96 | 1 | 0.56 | 30 | 78 | 100 | 100 | 100 | 100 | | |

TABLE IV-continued

| | | | | % PLANT INHIBITION AND % SAFENING EFFECT ( ) | | | | | | | |
|---|---|---|---|---|---|---|---|---|---|---|---|
| HERBICIDE | | ANTIDOTE | | CORN | | GREEN FOXTAIL | | BARNYARD GRASS | | CRAB GRASS | |
| No. | RATE | No. | RATE | W | WO | W | WO | W | WO | W | WO |
| 5 | 8.96 | 1 | 0.56 | 25 | 95 | 100 | 100 | 100 | 100 | | |
| | | | | (61) | | (0) | | (0) | | | |
| 5 | 8.96 | 1 | 0.56 | 73 | 85 | 100 | 100 | 100 | 100 | | |
| | | | | (73) | | (0) | | (0) | | | |
| 5 | 8.96 | 1 | 0.56 | 75 | 95 | 100 | 100 | 100 | 100 | | |
| | | | | (14) | | (0) | | (0) | | | |
| 5 | 8.96 | 1 | 0.56 | 10 | 45 | 100 | 100 | 100 | 100 | | |
| | | | | (21) | | (0) | | (0) | | | |
| 5 | 8.96 | 1 | 0.24 | 13 | 92 | 100 | 100 | 100 | 100 | | |
| | | | | (77) | | (0) | | (0) | | | |
| 5 | 8.96 | 1 | 2.24 | 38 | 95 | 100 | 100 | 100 | 100 | | |
| | | | | (85) | | (0) | | (0) | | | |
| 5 | 8.96 | 1 | 2.24 | 8 | 45 | 100 | 100 | 100 | 100 | | |
| | | | | (60) | | (0) | | (0) | | | |
| 5 | 8.96 | 1 | 2.24 | 73 | 85 | 100 | 100 | 100 | 100 | | |
| | | | | (82) | | (0) | | (0) | | | |
| 5 | 8.96 | 1 | 2.24 | 5 | 78 | 100 | 100 | 100 | 100 | | |
| | | | | (14) | | (0) | | (0) | | | |
| 5 | 8.96 | 1 | 2.24 | 80 | 95 | 100 | 100 | 100 | 100 | | |
| | | | | (93) | | (0) | | (0) | | | |
| 5 | 4.48 | 5 | 0.14 | 0 | 27 | 100 | 100 | 100 | 100 | | |
| | | | | (15) | | (0) | | (0) | | | |
| 5 | 4.48 | 5 | 0.56 | 0 | 27 | 100 | 100 | 100 | 100 | | |
| | | | | (100) | | (0) | | (0) | | | |
| 5 | 4.48 | 5 | 2.24 | 0 | 27 | 100 | 100 | 100 | 100 | | |
| | | | | (100) | | (0) | | (0) | | | |
| 5 | 6.72 | 5 | 0.14 | 8 | 37 | 100 | 100 | 100 | 100 | | |
| | | | | (100) | | (0) | | (0) | | | |
| 5 | 6.72 | 5 | 0.56 | 8 | 37 | 100 | 100 | 100 | 100 | | |
| | | | | (78) | | (0) | | (0) | | | |
| 5 | 6.72 | 5 | 2.24 | 8 | 37 | 100 | 100 | 100 | 100 | | |
| | | | | (78) | | (0) | | (0) | | | |
| 5 | 8.96 | 5 | 0.14 | 8 | 48 | 100 | 100 | 100 | 100 | | |
| | | | | (78) | | (0) | | (0) | | | |
| 5 | 8.96 | 5 | 0.56 | 18 | 48 | 100 | 100 | 100 | 100 | | |
| | | | | (83) | | (0) | | (0) | | | |
| 5 | 8.96 | 5 | 2.24 | 5 | 48 | 100 | 100 | 100 | 100 | | |
| | | | | (62) | | (0) | | (0) | | | |
| 5 | 4.48 | 8 | 0.14 | 28 | 55 | 100 | 100 | 100 | 100 | | |
| | | | | (89) | | (0) | | (0) | | | |
| 5 | 4.48 | 8 | 0.56 | 5 | 55 | 100 | 100 | 100 | 100 | | |
| | | | | (49) | | (0) | | (0) | | | |
| 5 | 4.48 | 8 | 2.24 | 0 | 55 | 100 | 100 | 100 | 100 | | |
| | | | | (90) | | (0) | | (0) | | | |
| 5 | 6.72 | 8 | 0.14 | 28 | 55 | 100 | 100 | 100 | 100 | | |
| | | | | (100) | | (0) | | (0) | | | |
| 5 | 6.72 | 8 | 0.56 | 10 | 55 | 100 | 100 | 100 | 100 | | |
| | | | | (49) | | (0) | | (0) | | | |
| 5 | 6.72 | 8 | 2.24 | 5 | 55 | 100 | 100 | 100 | 100 | | |
| | | | | (81) | | (0) | | (0) | | | |
| 5 | 8.96 | 8 | 0.14 | 35 | 57 | 100 | 100 | 100 | 100 | | |
| | | | | (90) | | (0) | | (0) | | | |
| 5 | 8.96 | 8 | 0.56 | 10 | 57 | 100 | 100 | 100 | 100 | | |
| | | | | (55) | | (0) | | (0) | | | |
| 5 | 8.96 | 8 | 2.24 | 5 | 57 | 100 | 100 | 100 | 100 | | |
| | | | | (82) | | (0) | | (0) | | | |
| 5 | 4.48 | 17 | 0.14 | 13 | 20 | 100 | 100 | 100 | 98 | | |
| | | | | (91) | | (0) | | (0) | | | |
| 5 | 4.48 | 17 | 0.56 | 0 | 20 | 100 | 100 | 98 | 98 | | |
| | | | | (35) | | (0) | | (0) | | | |
| 5 | 4.48 | 17 | 2.24 | 0 | 20 | 100 | 100 | 100 | 100 | | |
| | | | | (100) | | (0) | | (0) | | | |
| 5 | 6.72 | 17 | 0.14 | 8 | 55 | 100 | 100 | 100 | 100 | | |
| | | | | (100) | | (0) | | (0) | | | |
| 5 | 6.72 | 17 | 0.56 | 5 | 55 | 100 | 100 | 100 | 100 | | |
| | | | | (85) | | (0) | | (0) | | | |
| 5 | 6.72 | 17 | 2.24 | 0 | 55 | 100 | 100 | 100 | 100 | | |
| | | | | (90) | | (0) | | (0) | | | |
| 5 | 8.96 | 17 | 0.14 | 30 | 45 | 100 | 100 | 100 | 100 | | |
| | | | | (100) | | (0) | | (0) | | | |
| 5 | 8.96 | 17 | 0.56 | 20 | 45 | 100 | 100 | 100 | 100 | | |
| | | | | (33) | | (0) | | (0) | | | |
| 5 | 8.96 | 17 | 2.24 | 5 | 45 | 100 | 100 | 100 | 100 | | |
| | | | | (38) | | (0) | | (0) | | | |
| 6 | 0.56 | 1 | 0.14 | 0 | 98 | 100 | 100 | 100 | 100 | | |
| | | | | (88) | | (0) | | (0) | | | |
| | | | | (100) | | (0) | | (0) | | | |

TABLE IV-continued

| | | | | % PLANT INHIBITION AND % SAFENING EFFECT ( ) | | | | | | | |
|---|---|---|---|---|---|---|---|---|---|---|---|
| HERBICIDE | | ANTIDOTE | | CORN | | GREEN FOXTAIL | | BARNYARD GRASS | | CRAB GRASS | |
| No. | RATE | No. | RATE | W | WO | W | WO | W | WO | W | WO |
| 6 | 0.56 | 1 | 0.14 | 10 (83) | 62 | 90 (5) | 95 | 100 (0) | 100 | 100 (0) | 98 |
| 6 | 0.56 | 1 | 0.56 | 10 (89) | 98 | 98 (2) | 100 | 100 (0) | 100 | | |
| 6 | 0.56 | 1 | 0.56 | 0 (100) | 62 | 98 (0) | 95 | 100 (0) | 100 | 55 (43) | 98 |
| 6 | 0.56 | 1 | 2.24 | 0 (100) | 98 | 100 (0) | 100 | 100 (0) | 100 | | |
| 6 | 0.56 | 1 | 2.24 | 0 (100) | 62 | 98 (0) | 95 | 100 (0) | 100 | 50 (48) | 98 |
| 6 | 1.12 | 1 | 0.14 | 5 (94) | 90 | 100 (0) | 100 | 100 (0) | 100 | | |
| 6 | 1.12 | 1 | 0.14 | 0 (100) | 45 | 100 (0) | 98 | 95 (0) | 95 | | |
| 6 | 1.12 | 1 | 0.14 | 20 (55) | 45 | 98 (0) | 95 | 98 (2) | 100 | | |
| 6 | 1.12 | 1 | 0.14 | 0 (100) | 27 | 95 (3) | 98 | 100 (0) | 100 | | |
| 6 | 1.12 | 1 | 0.14 | 25 (67) | 77 | 100 (0) | 98 | 100 (0) | 100 | 100 (0) | 100 |
| 6 | 1.12 | 1 | 0.14 | 45 (54) | 98 | 100 (0) | 100 | 100 (2) | 100 | | |
| 6 | 1.12 | 1 | 0.14 | 13 (86) | 93 | 100 (0) | 100 | 100 (0) | 100 | | |
| 6 | 1.12 | 1 | 0.56 | 0 (100) | 45 | 100 (0) | 98 | 95 (0) | 95 | | |
| 6 | 1.12 | 1 | 0.56 | 0 (100) | 90 | 100 (0) | 100 | 100 (0) | 100 | | |
| 6 | 1.12 | 1 | 0.56 | 8 (70) | 27 | 98 (0) | 98 | 100 (0) | 100 | | |
| 6 | 1.12 | 1 | 0.56 | 0 (100) | 45 | 98 (0) | 95 | 98 (2) | 100 | | |
| 6 | 1.12 | 1 | 0.56 | 8 (89) | 77 | 100 (0) | 98 | 100 (0) | 100 | 98 (2) | 100 |
| 6 | 1.12 | 1 | 0.56 | 0 (100) | 98 | 100 (0) | 100 | 100 (0) | 100 | | |
| 6 | 1.12 | 1 | 0.56 | 5 (94) | 93 | 100 (0) | 100 | 100 (0) | 100 | | |
| 6 | 1.12 | 1 | 2.24 | 0 (100) | 90 | 100 (0) | 100 | 100 (0) | 100 | | |
| 6 | 1.12 | 1 | 2.24 | 0 (100) | 27 | 98 (0) | 98 | 100 (0) | 100 | | |
| 6 | 1.12 | 1 | 2.24 | 0 (100) | 98 | 100 (0) | 100 | 100 (0) | 100 | | |
| 6 | 1.12 | 1 | 2.24 | 0 (100) | 93 | 100 (0) | 100 | 100 (0) | 100 | | |
| 6 | 1.12 | 1 | 2.24 | 0 (100) | 77 | 100 (0) | 98 | 100 (0) | 100 | 95 (5) | 100 |
| 6 | 1.12 | 1 | 2.24 | 0 (100) | 45 | 100 (0) | 95 | 98 (2) | 100 | | |
| 6 | 1.12 | 1 | 2.24 | 8 (82) | 45 | 98 (0) | 98 | 98 (0) | 95 | | |
| 6 | 2.24 | 1 | 0.14 | 33 (61) | 85 | 100 (0) | 100 | 100 (0) | 100 | | |
| 6 | 2.24 | 1 | 0.14 | 55 (43) | 98 | 100 (0) | 100 | 100 (0) | 100 | | |
| 6 | 2.24 | 1 | 0.14 | 0 (100) | 73 | 100 (0) | 100 | 98 (0) | 98 | | |
| 6 | 2.24 | 1 | 0.14 | 40 (56) | 92 | 100 (0) | 98 | 100 (0) | 100 | 98 (2) | 100 |
| 6 | 2.24 | 1 | 0.14 | 15 (81) | 82 | 100 (0) | 100 | 100 (0) | 100 | | |
| 6 | 2.24 | 1 | 0.14 | 30 (62) | 80 | 100 (0) | 100 | 100 (0) | 100 | | |
| 6 | 2.24 | 1 | 0.14 | 20 (53) | 43 | 100 (0) | 100 | 100 (0) | 100 | | |
| 6 | 2.24 | 1 | 0.56 | 0 (100) | 73 | 100 (0) | 100 | 95 (3) | 98 | | |
| 6 | 2.24 | 1 | 0.56 | 20 (79) | 98 | 100 (0) | 100 | 100 (0) | 100 | | |
| 6 | 2.24 | 1 | 0.56 | 3 (96) | 80 | 100 (0) | 100 | 100 (0) | 100 | | |
| 6 | 2.24 | 1 | 0.56 | 5 (94) | 85 | 100 (0) | 100 | 100 (0) | 100 | | |
| 6 | 2.24 | 1 | 0.56 | 17 (81) | 92 | 100 (0) | 98 | 100 (0) | 100 | 100 (0) | 100 |
| 6 | 2.24 | 1 | 0.56 | 23 | 82 | 100 | 100 | 100 | 100 | | |

TABLE IV-continued

| | | | | % PLANT INHIBITION AND % SAFENING EFFECT ( ) | | | | | | | |
|---|---|---|---|---|---|---|---|---|---|---|---|
| HERBICIDE | | ANTIDOTE | | CORN | | GREEN FOXTAIL | | BARNYARD GRASS | | CRAB GRASS | |
| No. | RATE | No. | RATE | W | WO | W | WO | W | WO | W | WO |
| | | | | (71) | | (0) | | (0) | | | |
| 6 | 2.24 | 1 | 0.56 | 8 | 43 | 98 | 100 | 100 | 100 | | |
| | | | | (81) | | (2) | | (0) | | | |
| 6 | 2.24 | 1 | 2.24 | 10 | 80 | 100 | 100 | 100 | 100 | | |
| | | | | (87) | | (0) | | (0) | | | |
| 6 | 2.24 | 1 | 2.24 | 8 | 98 | 100 | 100 | 100 | 100 | | |
| | | | | (91) | | (0) | | (0) | | | |
| 6 | 2.24 | 1 | 2.24 | 8 | 92 | 100 | 98 | 98 | 100 | 100 | 100 |
| | | | | (91) | | (0) | | (2) | | (0) | |
| 6 | 2.24 | 1 | 2.24 | 13 | 85 | 100 | 100 | 100 | 100 | | |
| | | | | (84) | | (0) | | (0) | | | |
| 6 | 2.24 | 1 | 2.24 | 0 | 73 | 98 | 100 | 95 | 98 | | |
| | | | | (100) | | (2) | | (3) | | | |
| 6 | 2.24 | 1 | 2.24 | 0 | 43 | 100 | 100 | 100 | 100 | | |
| | | | | (100) | | (0) | | (0) | | | |
| 6 | 2.24 | 1 | 2.24 | 10 | 82 | 100 | 100 | 100 | 100 | | |
| | | | | (87) | | (0) | | (0) | | | |
| 6 | 4.48 | 1 | 0.14 | 80 | 93 | 100 | 100 | 100 | 100 | | |
| | | | | (13) | | (0) | | (0) | | | |
| 6 | 4.48 | 1 | 0.14 | 95 | 73 | 100 | 100 | 100 | 100 | | |
| | | | | (0) | | (0) | | (0) | | | |
| 6 | 4.48 | 1 | 0.14 | 95 | 98 | 100 | 100 | 100 | 100 | | |
| | | | | (3) | | (0) | | (0) | | | |
| 6 | 4.48 | 1 | 0.14 | 13 | 68 | 100 | 98 | 100 | 100 | | |
| | | | | (80) | | (0) | | (0) | | | |
| 6 | 4.48 | 1 | 0.14 | 43 | 90 | 100 | 100 | 100 | 100 | | |
| | | | | (52) | | (0) | | (0) | | | |
| 6 | 4.48 | 1 | 0.56 | 58 | 73 | 100 | 100 | 100 | 100 | | |
| | | | | (20) | | (0) | | (0) | | | |
| 6 | 4.48 | 1 | 0.56 | 30 | 68 | 100 | 98 | 100 | 100 | | |
| | | | | (55) | | (0) | | (0) | | | |
| 6 | 4.48 | 1 | 0.56 | 38 | 98 | 100 | 100 | 100 | 100 | | |
| | | | | (61) | | (0) | | (0) | | | |
| 6 | 4.48 | 1 | 0.56 | 18 | 90 | 100 | 100 | 100 | 100 | | |
| | | | | (80) | | (0) | | (0) | | | |
| 6 | 4.48 | 1 | 0.56 | 33 | 93 | 100 | 100 | 100 | 100 | | |
| | | | | (64) | | (0) | | (0) | | | |
| 6 | 4.48 | 1 | 2.24 | 45 | 90 | 100 | 100 | 100 | 100 | | |
| | | | | (50) | | (0) | | (0) | | | |
| 6 | 4.48 | 1 | 2.24 | 18 | 73 | 100 | 100 | 100 | 100 | | |
| | | | | (75) | | (0) | | (0) | | | |
| 6 | 4.48 | 1 | 2.24 | 30 | 93 | 100 | 100 | 100 | 100 | | |
| | | | | (67) | | (0) | | (0) | | | |
| 6 | 4.48 | 1 | 2.24 | 30 | 98 | 100 | 100 | 100 | 100 | | |
| | | | | (69) | | (0) | | (0) | | | |
| 6 | 4.48 | 1 | 2.24 | 5 | 68 | 100 | 98 | 100 | 100 | | |
| | | | | (92) | | (0) | | (0) | | | |
| 6 | 0.56 | 5 | 0.14 | 80 | 98 | 98 | 100 | 100 | 100 | | |
| | | | | (18) | | (2) | | (0) | | | |
| 6 | 0.56 | 5 | 0.56 | 0 | 98 | 100 | 100 | 100 | 100 | | |
| | | | | (100) | | (0) | | (0) | | | |
| 6 | 0.56 | 5 | 2.24 | 0 | 98 | 100 | 100 | 100 | 100 | | |
| | | | | (100) | | (0) | | (0) | | | |
| 6 | 1.12 | 5 | 0.14 | 88 | 98 | 100 | 100 | 100 | 100 | | |
| | | | | (10) | | (0) | | (0) | | | |
| 6 | 1.12 | 5 | 0.56 | 58 | 98 | 100 | 100 | 100 | 100 | | |
| | | | | (40) | | (0) | | (0) | | | |
| 6 | 1.12 | 5 | 0.56 | 8 | 98 | 100 | 100 | 100 | 100 | | |
| | | | | (91) | | (0) | | (0) | | | |
| 6 | 2.24 | 5 | 0.14 | 95 | 98 | 100 | 100 | 100 | 100 | | |
| | | | | (3) | | (0) | | (0) | | | |
| 6 | 2.24 | 5 | 0.56 | 85 | 98 | 100 | 100 | 100 | 100 | | |
| | | | | (13) | | (0) | | (0) | | | |
| 6 | 2.24 | 5 | 2.24 | 43 | 98 | 100 | 100 | 100 | 100 | | |
| | | | | (56) | | (0) | | (0) | | | |
| 6 | 0.56 | 8 | 0.14 | 23 | 82 | 95 | 100 | 100 | 100 | | |
| | | | | (71) | | (5) | | (0) | | | |
| 6 | 0.56 | 8 | 0.56 | 0 | 82 | 98 | 100 | 100 | 100 | | |
| | | | | (100) | | (2) | | (0) | | | |
| 6 | 0.56 | 8 | 2.24 | 0 | 82 | 100 | 100 | 100 | 100 | | |
| | | | | (100) | | (0) | | (0) | | | |
| 6 | 1.12 | 8 | 0.14 | 58 | 88 | 100 | 95 | 100 | 100 | | |
| | | | | (34) | | (0) | | (0) | | | |
| 6 | 1.12 | 8 | 0.14 | 33 | 85 | 100 | 100 | 100 | 100 | | |
| | | | | (61) | | (0) | | (0) | | | |
| 6 | 1.12 | 8 | 0.14 | 18 | 45 | 95 | 98 | 95 | 95 | | |
| | | | | (60) | | (3) | | (0) | | | |

TABLE IV-continued
% PLANT INHIBITION AND % SAFENING EFFECT ( )

| HERBICIDE | | ANTIDOTE | | CORN | | GREEN FOXTAIL | | BARNYARD GRASS | | CRAB GRASS | |
|---|---|---|---|---|---|---|---|---|---|---|---|
| No. | RATE | No. | RATE | W | WO | W | WO | W | WO | W | WO |
| 6 | 1.12 | 8 | 0.56 | 0 (100) | 88 | 100 (0) | 95 | 100 (0) | 100 | | |
| 6 | 1.12 | 8 | 0.56 | 0 (100) | 85 | 100 (0) | 100 | 100 (0) | 100 | | |
| 6 | 1.12 | 8 | 0.56 | 5 (88) | 45 | 95 (3) | 98 | 95 (0) | 95 | | |
| 6 | 1.12 | 8 | 2.24 | 0 (100) | 85 | 98 (2) | 100 | 100 (0) | 100 | | |
| 6 | 1.12 | 8 | 2.24 | 0 (100) | 45 | 95 (3) | 98 | 100 (0) | 95 | | |
| 6 | 1.12 | 8 | 2.24 | 0 (100) | 88 | 100 (0) | 95 | 98 (2) | 100 | | |
| 6 | 2.24 | 8 | 0.14 | 88 (0) | 83 | 100 (0) | 98 | 100 (0) | 100 | | |
| 6 | 2.24 | 8 | 0.14 | 38 (47) | 73 | 100 (0) | 100 | 95 (3) | 98 | | |
| 6 | 2.24 | 8 | 0.14 | 48 (46) | 90 | 100 (0) | 100 | 100 (0) | 100 | | |
| 6 | 2.24 | 8 | 0.56 | 23 (74) | 90 | 100 (0) | 100 | 100 (0) | 100 | | |
| 6 | 2.24 | 8 | 0.56 | 13 (82) | 73 | 100 (0) | 100 | 100 (0) | 98 | | |
| 6 | 2.24 | 8 | 0.56 | 33 (60) | 83 | 100 (0) | 98 | 100 (0) | 100 | | |
| 6 | 2.24 | 8 | 2.24 | 5 (94) | 90 | 100 (0) | 100 | 100 (0) | 100 | | |
| 6 | 2.24 | 8 | 2.24 | 0 (100) | 83 | 100 (0) | 98 | 100 (0) | 100 | | |
| 6 | 2.24 | 8 | 2.24 | 8 (89) | 73 | 100 (0) | 100 | 100 (0) | 100 | | |
| 6 | 4.48 | 8 | 0.14 | 95 (0) | 93 | 100 (0) | 100 | 100 (0) | 100 | | |
| 6 | 4.48 | 8 | 0.14 | 88 (12) | 100 | 100 (0) | 100 | 100 (0) | 100 | | |
| 6 | 4.48 | 8 | 0.56 | 58 (42) | 100 | 100 (0) | 100 | 100 (0) | 100 | | |
| 6 | 4.48 | 8 | 0.56 | 45 (51) | 93 | 100 (0) | 100 | 100 (0) | 100 | | |
| 6 | 4.48 | 8 | 2.24 | 13 (86) | 93 | 100 (0) | 100 | 100 (0) | 100 | | |
| 6 | 4.48 | 8 | 2.24 | 13 (87) | 100 | 100 (0) | 100 | 100 (0) | 100 | | |
| 6 | 1.12 | 12 | 0.14 | 25 (61) | 65 | 100 (0) | 100 | 100 (0) | 100 | | |
| 6 | 1.12 | 12 | 0.56 | 5 (92) | 65 | 100 (0) | 100 | 100 (0) | 100 | | |
| 6 | 1.12 | 12 | 2.24 | 0 (100) | 65 | 100 (0) | 100 | 100 (0) | 100 | | |
| 6 | 2.24 | 12 | 0.14 | 35 (47) | 67 | 100 (0) | 100 | 100 (0) | 100 | | |
| 6 | 2.24 | 12 | 0.56 | 20 (70) | 67 | 98 (2) | 100 | 100 (0) | 100 | | |
| 6 | 2.24 | 12 | 2.24 | 18 (73) | 67 | 100 (0) | 100 | 100 (0) | 100 | | |
| 6 | 4.48 | 12 | 0.14 | 58 (31) | 85 | 98 (2) | 100 | 100 (0) | 100 | | |
| 6 | 4.48 | 12 | 0.56 | 90 (0) | 85 | 100 (0) | 100 | 100 (0) | 100 | | |
| 6 | 4.48 | 12 | 2.24 | 18 (78) | 85 | 100 (0) | 100 | 100 (0) | 100 | | |
| 6 | 1.12 | 17 | 0.14 | 20 (78) | 93 | 100 (0) | 100 | 100 (0) | 100 | | |
| 6 | 1.12 | 17 | 0.56 | 15 (83) | 93 | 100 (0) | 100 | 98 (2) | 100 | | |
| 6 | 1.12 | 17 | 2.24 | 10 (89) | 93 | 100 (0) | 100 | 95 (5) | 100 | | |
| 6 | 2.24 | 17 | 0.14 | 63 (23) | 82 | 100 (0) | 100 | 100 (0) | 100 | | |
| 6 | 2.24 | 17 | 0.56 | 43 (47) | 82 | 100 (0) | 100 | 100 (0) | 100 | | |
| 6 | 2.24 | 17 | 2.24 | 0 (100) | 82 | 100 (0) | 100 | 100 (0) | 100 | | |
| 6 | 4.48 | 17 | 0.14 | 98 (0) | 73 | 100 (0) | 100 | 100 (0) | 100 | | |
| 6 | 4.48 | 17 | 0.56 | 58 (20) | 73 | 100 (0) | 100 | 100 (0) | 100 | | |
| 6 | 4.48 | 17 | 2.24 | 20 | 73 | 100 | 100 | 100 | 100 | | |

TABLE IV-continued

| | | | | % PLANT INHIBITION AND % SAFENING EFFECT ( ) | | | | | | | |
|---|---|---|---|---|---|---|---|---|---|---|---|
| HERBICIDE | | ANTIDOTE | | CORN | | GREEN FOXTAIL | | BARNYARD GRASS | | CRAB GRASS | |
| No. | RATE | No. | RATE | W | WO | W | WO | W | WO | W | WO |
| 6 | 1.12 | 18 | 0.14 | 8 (72) | 58 | 98 (0) | 98 | 95 (0) | 85 | | |
| 6 | 1.12 | 18 | 0.56 | 0 (86) | 58 | 98 (0) | 98 | 100 (0) | 85 | | |
| 6 | 1.12 | 18 | 2.24 | 13 (100) | 58 | 100 (0) | 98 | 98 (0) | 85 | | |
| 6 | 2.24 | 18 | 0.14 | 5 (77) | 80 | 100 (0) | 100 | 98 (0) | 90 | | |
| 6 | 2.24 | 18 | 0.56 | 0 (93) | 80 | 100 (0) | 100 | 98 (0) | 90 | | |
| 6 | 2.24 | 18 | 2.24 | 5 (100) | 80 | 100 (0) | 100 | 98 (0) | 90 | | |
| 6 | 4.48 | 18 | 0.14 | 63 (93) | 83 | 100 (0) | 100 | 100 (0) | 93 | | |
| 6 | 4.48 | 18 | 0.56 | 33 (24) | 83 | 100 (0) | 100 | 98 (0) | 93 | | |
| 6 | 4.48 | 18 | 2.24 | 10 (60) | 83 | 100 (0) | 100 | 100 (0) | 93 | | |
| | | | | (87) | | | | | | | |

The foregoing examples illustrate that the haloacyl 1-substituted-1,2,3,4-tetrahydroisoquinoline compounds of this invention are useful in reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjuction with an adjuvant in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of finely-divided sold carriers and extenders including suitable adjuvants are talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dipersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. The compositions can also be applied from aircraft as a dust or spray. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed.

Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating compositions or for antidotes applied to soil, suitable carriers may be either solids, such as talc, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks any may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate, and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10-18 carbon atoms, and condensation products of ethylene oxide with fatty acids, alkylphenols, and mercaptans.

The following examples describe preparation of herbicide formulations, antidote formulations, and herbicide+antidote formulations, and use of these formulations, under field test conditions.

EXAMPLE 26

An emulsifiable concentrate formulation containing antidote compound #1 was prepared with the following components:

|  | % by wt. |
|---|---|
| 2-(dichloroacetyl)-1-methyl-1,2,3,4-tetrahydro-isoquinoline (95% Tech.) | 22.06 |
| FLOMO 50H emulsifier (50 solution of calcium dodecylbenzene sulfonate in mineral spirits); De Soto Chemical Co., Chicago, Ill. | 4.00 |
| FLOMO 54C emulsifier (caster oil epoxylated with 54 moles ethylene oxide); De Soto Chemical Co., Chicago, Ill. | 6.00 |
| Monochlorobenzene solvent | 67.94 |

These components were mixed together at room temperature until a uniform blend was obtained. The formulation had a specific gravity of 1.1458 observed at 20° C. calculated against water at 15.6° C., and a solution point less than 0° C. The formulation showed very good bloom at water-hardness concentrations of 114 ppm, 342 ppm, and 1000 ppm. The emulsions were observed as 100 percent stable after one hour at each test concentration. The liquid formulation was dark brown in color and contained 21% antidote compound #1.

EXAMPLE 27

An emulsifiable concentrate formulation containing a prior art antidote compound, N-dichloroacetyl-1,2,3,4-tetrahydroisoquinoline, was prepared with the following components:

|  | % by wt. |
|---|---|
| N—dichloroacetyl-1,2,3,4-tetrahydroisoquinoline (prepared by procedures of Example 22) | 10.69 |
| GAFAC RE-610 emulsifier (mixture of mono- and di-phosphate esters of ethoxylated monyl phenol); GAF Corp., New York City | 5.00 |
| Monochlorobenzene solvent | 84.31 |

These components were mixed together at room temperature until a uniform blend was obtained. The formulation had a specific gravity of 1.1216 observed at 25° C. calculated against water at 15.6° C., a solution point of 11° C., and a flash point less than 38° C. The formulation showed very good bloom at concentrations in water of 114 ppm and 342 ppm, and good bloom at 1000 ppm. Emulsions were observed one hour after preparation as having a cream layer 1 cm in thickness at 114 ppm and 1.5 cm in thickness at 1000 ppm water-hardness concentrations.

EXAMPLE 28

An emulsifiable concentrate type formulation containing acetochlor (herbicide compound #5) was prepared containing the following components:

|  | % by wt. |
|---|---|
| Acetochlor (93.5% technical) | 92.00 |
| Witco C-5438 emulsifier (blended anionic/non-ionic ethylene glycol block copolymer); Witco Chemical Co., New York, N.Y. | 7.96 |
| GE AG-78 antifoaming agent (polysiloxane); General Electric Co., Waterford, N.Y. | 0.02 |
| Methyl violet dye; Dye Specialities Co., Jersey City, N.J. | 0.017 |

These components were mixed together at room temperature until a uniform blend was obtained. The formulation had a specific gravity of 1.1167 observed at 20° C. and calculated against water at 15.6° C., and had a flash point above 100° C. (tag closed-cup method). The formulation showed perfect emulsion bloom at water-hardness concentrations of 114 ppm, 342 ppm and 100 ppm. The emulsions were observed after one hour as 100 percent stable at each test concentration. The formulation was blue in color and contained 86.02% by weight of acetochlor.

EXAMPLE 29

An emulsifiable concentrate formulation containing the herbicide 2-chloro-2'-methyl-6'-methoxy-N-(isopropoxymethyl)acetanilide (herbicide compound #6) was prepared containing the following components:

|  | % by wt. |
|---|---|
| 2-chloro-2'-methyl-6'-methoxy-N—(isopropoxymethyl)acetanilide (78% Tech.) | 41.16 |
| FLOMO 50H emulsifier (50% solution of calcium dodecylbenzene sulfonate in mineral spirits); De Soto Chemical Co., Chicago, Ill. | 1.79 |
| FLOMO 14D emulsifier (reaction product of dodecyl phenol and 14 mols ethylene oxide); De Soto Chemical Co., Chicago, Ill. | 1.91 |
| FLOMO XH emulsifier (block copolymer of propylene oxide and ethylene oxide); De Soto Chemical Co., Chicago, Ill. | 0.93 |
| FLOMO 54C emulsifier (caster oil epoxylated with 54 moles ethylene oxide); De Soto Chemical Co., Chicago, Ill. | 0.17 |
| Naphtha Solvent | 0.20 |
| Monochlorobenzene Solvent | 53.84 |

These components were mixed together at room temperature until a uniform blend was obtained. The formulation had a specific gravity of 1.1213 observed at 25° C. and calculated against water at 15.6° C., a solution point at 2° C., and a flash point less than 38° C. The formulation showed perfect emulsion bloom at water-hardness concentrations of 114 ppm, 342 ppm, and very good bloom at 1000 ppm. The emulsions were observed as 100 percent stable after one hour at each test concentration. The liquid formulation was white in color and contained 32.1% by weight of herbicide compound #6.

EXAMPLE 30

Tank mix formulations were prepared for field testing to determine the comparative effects of herbicide alone, herbicide-and-antidote in combination, and antidote alone. For each formulation, a tractor-mounted 20-liter spray tank was filled about half-full with water. For the herbicide formulations containing no antidote, an appropriate amount of emulsifiable concentrate, such as prepared in Examples 28 or 29, was added directly to a tank. For the antidote-containing formulations, the antidote emulsifiable-concentrate form as prepared in Example 26 or 27, was added to a tank. The for the herbicide+antidote formulation, herbicide emulsifiable concentrate was added to a tank containing antidote. Each tank-mix formulation was agitated sufficiently to ensure a uniform suspension. The relative amounts of water, herbicide emulsifiable concentrate, or antidote, added to the tank were calculated for each formulation based upon a formulation spraying rate of 281 l/ha (30 gal/acre) in order to achieve various field application rates of herbicide and antidote, as appropriate, for the rates shown in Tables V-IX. For the field tests of Examples 31-33 each formulation was sprayed on three replicate plots, about 4 m×9 m (12 ft×30 ft) in area, with a small-plot tractor-mounted sprayer. The plots were selected in a random manner in order to normalize variations in plot soil conditions. Three control plots were established which were not treated with herbicide or with antidote formulations.

EXAMPLE 31

Formulations of acetochlor (herbicide compound #5) and tank-mix safened acetochlor using antidote compound #1 were applied to side-by-side field plots to determine their relative inhibition of the grassy weed giant foxtail in the presence of corn in southern Illinois. The side-by-side comparison included plots treated by "pre-emergence" application method ("PRE") and by pre-plant incorporation method ("PPI"). Field test plots were prepared from silty clay loam topsoil containing approximately 4% organic matter. Test formulations of acetochlor, safened acetochlor, and a control formulation of antidote without herbicide, were prepared and sprayed on field plots as described in Example 30. For the pre-plant incorporated application method, a Ferguson Tilrovator was used to incorporate the sprayed formulation to a depth of about 2.5 cm (1 in). A four-row John Deere Maxi-Merge planter was used to plant 12 rows of Pioneer 3320 corn seed to a depth of about 3 cm (1¼ in) at a seeding rate of about 138,000 seed/ha (56,000 seed/ac). Test observations are reported in Table V.

Field Conditions at Treatment:
Wind speed: 16-48 Km/hr (10-30 mph), gusty
Air temperature: 22° C. (71° F.)
Soil temperature: 18° C. (65° F.)
Soil moisture: dry @ surface; moist @ seed depth.
Rainfall/Irrigation:
First significant rainfall: 0.6 cm (0.23 in) on day of treatment
Rainfall (first 3 weeks): 4.95 cm (1.98 in)
Irrigation: none

TABLE V

| Formulation* | | Crop/Weed Inhibition (%) | | | |
|---|---|---|---|---|---|
| | | Corn | | Giant Foxtail | |
| Herbicide # | Antidote #1 | a PRE/PPI | b PRE/PPI | a PRE/PPI | b PRE/PPI |
| 0 | 0 | 0/0 | 0/0 | 0/0 | 0/0 |
| Herbicide #3 | | | | | |
| 2.24 | 0 | 7/13 | 3/3 | 88/97 | 78/78 |
| 4.48 | 0 | 13/18 | 10/10 | 96/98 | 87/87 |
| 6.72 | 0 | 17/20 | 7/12 | 100/100 | 94/94 |
| Herbicide #5 | | | | | |
| 2.24 | 0.11 | 13/20 | 7/15 | 98/99 | 93/93 |
| 4.48 | 0.22 | 15/20 | 13/15 | 99/100 | 97/99 |
| 6.72 | 0.34 | 25/27 | 15/20 | 100/100 | 99/99 |
| Herbicide #5 + Antidote #1 | | | | | |
| 2.24 | 0.15 | 8/13 | 2/12 | 96/100 | 92/98 |
| 4.48 | 0.30 | 15/15 | 10/12 | 99/100 | 97/98 |
| 6.72 | 0.45 | 23/18 | 15/18 | 100/100 | 96/99 |
| 2.24 | 0.22 | 10/8 | 5/8 | 98/100 | 90/95 |
| 4.48 | 0.45 | 13/12 | 8/12 | 99/100 | 96/99 |
| 6.72 | 0.67 | 20/15 | 8/12 | 100/100 | 98/100 |
| 0 | 1.67 | 3/7 | | 0/0 | |

*Application rate in Kg/ha of herbicide and antidote.
a = Observations taken at 23 days after treatment.
b = Observations taken at 58 days after treatment.

Comparative field tests were made between prior art and invention antidote compounds to determine the relative efficacy of the two antidotes for safening acetochlor used for weed control in corn. The comparison was made between tank-mix formulations containing acetochlor, and safened-acetochlor, using the following antidotes:

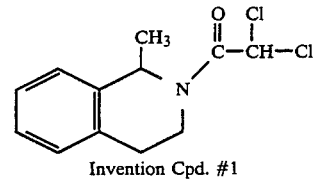

Invention Cpd. #1

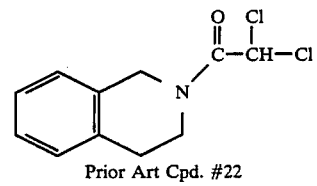

Prior Art Cpd. #22

Example 32 and 33 describe the field test conditions for the comparative tests carried out at two different locations in eastern Missouri.

EXAMPLE 32

Formulations of acetochlor (herbicide compound #5) and two tank-mix safened acetochlor formulations containing different antidotes (compounds #1 and 22) were applied to side-by-side field plots to determine their relative inhibition of the broadleaf weeds ivy leaf morningglory and common purslane in the presence of corn in eastern Missouri. The side-by-side comparisons included plots treated by pre-emergence application method ("PRE") and by preplant-incorporated method ("PPI"). Field test plots were prepared from silt loam topsoil containing approximately 1% organic matter. Test formulations of acetochlor, safened acetochlor, and a control formulation of antidote without herbicide, were prepared and sprayed on field plots as described in Example 30. For the pre-plant incorporated application method, a Ferguson Tilrovator was used to incorporate the sprayed formulations to a depth of about 2.5 cm (1 in.). A four-row John Deere Maxi-Merge planter was used to plant 8 rows of Pioneer 3320 corn seed to a depth of about 3 cm (1¼ in) at a seeding rate of about 138,000 seed/ha (56,000 seed/ac). Test observations are reported in Table VI.

Field Conditions at Treatment
Wind speed: 8–16 Km/hr (5–10 mph)
Air temperature: 23° C. (73° F.)
Soil temperature: 23° C. (73° F.)
Soil moisture: dry @ surface; moist @ seed depth.
Rainfall/Irrigation:
First significant rainfall: 2.16 cm (0.85 in) 4 days after treatment.
Rainfall (first 3 weeks): 16.2 cm (6.37 in)
Irrigation: 2.5 cm (1.0 in) 2 days after treatment.

side comparisons included plots treated by pre-emergence application method ("PRE") and by pre-plant-incorporated method ("PPI"). Field test plots were prepared from silt loam topsoil containing approximately 1% organic matter. Test formulations of acetochlor, safened acetochlor, and a control formulation of antidote without herbicide, were prepared and sprayed on field plots as described in Example 30. For the pre-plant incorporated application method, a Ferguson Tilrovator was used to incorporate the sprayed formulations to a depth of about 2.5 cm (1 in.). A four-row John Deere Maxi-Merge planter was used to plant 8 rows of Pioneer 3320 corn seed to a depth of about 3 cm (1¼ in) at a seeding rate of about 138,000 seed/ha (56,000 seed/ac). Test observations are reported in Table VII.

Field Conditions at Treatment
Wind speed: 0–8 Km/hr (0–5 mph)

TABLE VI

| Formulation* | | Crop/Weed Inhibition (%) | | | |
|---|---|---|---|---|---|
| | | Corn | | Ivy Leaf Morningglory | Common Purslane |
| Herbicide # | Antidote #1 or #22 | a PRE/PPI | b PRE/PPI | a PRE/PPI | b PRE/PPI |
| 0 | 0 | 0 | 0 | 0 | 0 |
| *Herbicide #3* | | | | | |
| 2.24 | 0 | 12/18 | 8/12 | 20/23 | 92/52 |
| 4.48 | 0 | 17/22 | 12/28 | 48/70 | 99/75 |
| 6.72 | 0 | 25/32 | 32/40 | 72/77 | 100/95 |
| *Herbicide #5* | | | | | |
| 2.24 | 0 | 32/47 | 28/43 | 48/63 | 98/73 |
| 4.48 | 0 | 68/73 | 57/68 | 77/87 | 100/96 |
| 6.72 | 0 | 83/87 | 82/78 | 96/94 | 100/100 |
| *Herbicide #5 + Antidote #1* | | | | | |
| 2.24 | 0.11 | 17/17 | 15/20 | 47/62 | 99/85 |
| 4.48 | 0.22 | 22/18 | 30/30 | 78/87 | 100/94 |
| 6.72 | 0.34 | 28/25 | 38/40 | 92/94 | 100/99 |
| 2.24 | 0.15 | 13/12 | 13/17 | 48/63 | 99/83 |
| 4.48 | 0.30 | 17/18 | 22/20 | 78/87 | 100/96 |
| 6.72 | 0.45 | 23/20 | 35/28 | 92/93 | 100/99 |
| 2.24 | 0.22 | 8/8 | 13/15 | 48/62 | 99/88 |
| 4.48 | 0.45 | 12/12 | 17/17 | 78/87 | 100/94 |
| 6.72 | 0.67 | 17/13 | 27/25 | 92/92 | 100/98 |
| 0 | 0.67 | 0/0 | 0/0 | 0/0 | 0/0 |
| *Herbicide #5 + Antidote #22* | | | | | |
| 2.24 | 0.11 | 20/27 | 30/35 | 47/62 | 98/88 |
| 4.48 | 0.22 | 42/35 | 43/48 | 77/88 | 100/97 |
| 6.72 | 0.34 | 65/45 | 60/53 | 96/92 | 100/99 |
| 2.24 | 0.15 | 17/18 | 25/32 | 48/63 | 99/89 |
| 4.48 | 0.30 | 35.23 | 35/37 | 75/83 | 100/98 |
| 6.72 | 0.45 | 58/38 | 53/45 | 94/93 | 100/99 |
| 2.24 | 0.22 | 17/20 | 25/30 | 47/63 | 100/88 |
| 4.48 | 0.45 | 28/23 | 33/35 | 77/82 | 100/92 |
| 6.72 | 0.67 | 52.32 | 43/43 | 93/93 | 100/99 |
| 0 | 0.67 | 0/0 | 0/2 | 0/0 | 0/0 |

*Application rate in Kg/ha for herbicide and antidote.
a = Observations taken at 19 days after treatment.
b = Observations taken at 29 days after treatment.

EXAMPLE 33

Formulations of acetochlor (herbicide compound #5) and two tank-mix safened acetochlor formulations containing different antidotes (compounds #1 and 22) were applied to side-by-side field plots to determine their relative inhibition of the broadleaf weed Velvetleaf in the presence of corn in eastern Missouri. The side-by- Air temperature: 25.5° C. (78° F.)
Soil temperature: 25.5° C. (78° F.)
Soil moisture: dry @ surface; moist @ seed depth.
Rainfall/Irrigation:
First significant rainfall: 1.63 cm (0.64 in) 8 days after treatment.
Rainfall (first 3 weeks): 18.9 cm (7.43 in)
Irrigation: 2.5 cm (1.0 in) 2 days after treatment.

TABLE VII

| Formulation* | | Crop/Weed Inhibition (%) | | | |
|---|---|---|---|---|---|
| | | Corn | | Velvetleaf | |
| Herbicide # | Antidote #1 or #22 | a PRE/PPI | b PRE/PPI | a PRE/PPI | b PRE/PPI |
| 0 | 0 | 0 | 0 | 0 | 0 |

TABLE VII-continued

| Formulation* | | Crop/Weed Inhibition (%) | | | |
|---|---|---|---|---|---|
| | | Corn | | Velvetleaf | |
| Herbicide # | Antidote #1 or #22 | a PRE/PPI | b PRE/PPI | a PRE/PPI | b PRE/PPI |
| Herbicide #3 | | | | | |
| 2.24 | 0 | 7/13 | 5/10 | 30/47 | 63/67 |
| 4.48 | 0 | 13/20 | 10/15 | 48/78 | 87/98 |
| 6.72 | 0 | 30/32 | 30/30 | 68/88 | 90/98 |
| Herbicide #5 | | | | | |
| 2.24 | 0 | 28/37 | 20/35 | 72/85 | 83/87 |
| 4.48 | 0 | 58/63 | 45/65 | 87/96 | 92/100 |
| 6.72 | 0 | 78/82 | 68/72 | 97/97 | 100/100 |
| Herbicide #5 + Antidote #1 | | | | | |
| 2.24 | 0.11 | 17/10 | 12/12 | 67/88 | 88/90 |
| 4.48 | 0.22 | 27/20 | 22/22 | 87/97 | 93/100 |
| 6.72 | 0.34 | 33/20 | 35/28 | 96/100 | 98/100 |
| 2.24 | 0.15 | 12/10 | 10/8 | 68/88 | 90/97 |
| 4.48 | 0.30 | 18/12 | 18/12 | 87/97 | 97/100 |
| 6.72 | 0.45 | 32/18 | 33/20 | 95/100 | 100/100 |
| 2.24 | 0.22 | 8/8 | 8/5 | 72/85 | 95/97 |
| 4.48 | 0.45 | 17/12 | 18/10 | 87/96 | 98/100 |
| 6.72 | 0.67 | 27/15 | 28/17 | 96/100 | 99/100 |
| 0 | 0.67 | 0/0 | 2/0 | 0/0 | 0/0 |
| Herbicide #5 + Antidote #22 | | | | | |
| 2.24 | 0.11 | 22/17 | 23/15 | 72/88 | 92/97 |
| 4.48 | 0.22 | 43/32 | 48/35 | 88/97 | 88/97 |
| 6.72 | 0.34 | 58/38 | 58/40 | 98/100 | 98/99 |
| 2.24 | 0.15 | 18/10 | 20/13 | 73/87 | 90/96 |
| 4.48 | 0.30 | 32/23 | 37/28 | 89/94 | 90/100 |
| 6.72 | 0.45 | 43/32 | 50/33 | 95/100 | 100/99 |
| 2.24 | 0.22 | 13/12 | 17/12 | 75/88 | 88/98 |
| 4.48 | 0.45 | 25/22 | 27/25 | 91/94 | 95/98 |
| 6.72 | 0.67 | 40/33 | 45/33 | 98/100 | 97/100 |
| 0 | 0.67 | 0/0 | 8/3 | 0/0 | 0/0 |

*Application rate in Kg/ha for herbicide and antidote.
a = Observations taken at 21 days after treatment.
b = Observations taken at 35 days after treatement.

The results of the comparative tests of Examples 32 and 33 show the invention antidote compound (Cpd. No. 1) as having consistently superior efficacy over the prior art antidote compound (Cpd. #22) in safening acetochlor in corn. Tables VIII and IX, below, report the corn injury data from Examples 32 and 33, respectively, taken at two different field locations in eastern Missouri. The data shown in parentheses are "% Safening Effect" calculated from the corn injury data by the formula described just before Example 23. Also given are the averaged safening effects for the pre-emergent and pre-plant-incorporated treatments. These averaged safening effects were used to determine the "Relative Efficacy" of the two antidotes by dividing the safening effect of the invention antidote compound (Cpd. #1) by the prior art antidote compound (Cpd. #22). The invention compound had superior efficacy to the prior art compound by factor ranging from 1.4 to 6.4 depending on the acetochlor+antidote use rates. Data averaged from both field locations show overall that the invention compound is more than twice as effective as the prior art antidote.

TABLE VIII

Invention vs. Prior Art Antidotes:
Safening Effect on Acetochlor in Corn at First Field Location

| Herbicide Rate (Kg/ha) | Antidote Rate (Kg/ha) | Acetochlor + Antidote #1* | | | | Acetochlor + Antidote #22* | | | | Safening Effect Ratio** |
|---|---|---|---|---|---|---|---|---|---|---|
| | | % Corn Injury | | Safening Effect (% Ave.) | | % Corn Injury | | Safening Effect (% Ave.) | | |
| | | PRE | | PPI | | PRE | | PPI | | |
| | | W WO | W WO | | | W WO | W WO | | | |
| 2.24 | 0.11 | 15 28 (46) | 20 43 (53) | 17.5 35.5 (51) | | 30 28 (0) | 35 43 (19) | 32.5 35.5 (8) | | 6.4 |
| 4.48 | 0.22 | 30 57 (47) | 30 68 (56) | 30 62.5 (52) | | 43 57 (25) | 48 68 (29) | 45.5 62.5 (27) | | 1.9 |
| 6.72 | 0.34 | 38 82 (54) | 40 78 (49) | 39 80 (51) | | 60 82 (27) | 53 78 (32) | 56.6 80 (29) | | 1.8 |
| 2.24 | 0.15 | 13 28 (54) | 17 43 (60) | 15 35.5 (58) | | 25 28 (11) | 32 43 (26) | 28.5 35.5 (20) | | 2.9 |
| 4.48 | 0.30 | 22 57 (61) | 20 68 (71) | 21 62.5 (66) | | 35 57 (39) | 37 68 (46) | 36 62.5 (42) | | 1.6 |
| 6.72 | 0.45 | 35 82 (57) | 28 78 (64) | 31.5 80 (61) | | 53 82 (35) | 45 78 (42) | 49 80 (39) | | 1.6 |
| 2.24 | 0.22 | 13 28 (54) | 15 43 (65) | 14 35.5 (60) | | 25 28 (11) | 30 43 (30) | 27.5 35.5 (23) | | 2.7 |
| 4.48 | 0.45 | 17 57 (70) | 17 68 (75) | 17 62.5 (73) | | 33 57 (39) | 35 68 (49) | 34 62.5 (46) | | 1.6 |
| 6.72 | 0.67 | 27 82 | 25 87 | 26 84.5 | | 43 82 | 43 78 | 43 80 | | |

TABLE VIII-continued

Invention vs. Prior Art Antidotes:
Safening Effect on Acetochlor in Corn at First Field Location

| Herbicide Rate (Kg/ha) | Antidote Rate (Kg/ha) | Acetochlor + Antidote #1* | | | | Acetochlor + Antidote #22* | | | | Safening Effect Ratio** |
|---|---|---|---|---|---|---|---|---|---|---|
| | | % Corn Injury | | | Safening Effect (% Ave.) | % Corn Injury | | | Safening Effect (% Ave.) | |
| | | PRE | | PPI | | PRE | | PPI | | |
| | | W WO | | W WO | | W WO | | W WO | | |
| | | (67) | | (68) | | (69) | (48) | | (45) | (46) | 1.5 |

*Observation taken at 29 days after treatment
**Safening Effect of Invention Cpd. #1 divided by Safening Effect of Prior Art Cpd. #22; average of all safening effect ratios is 2.4

TABLE IX

Invention vs. Prior Art Antidotes:
Safening Effect on Acetochlor in Corn at Second Field Location

| Herbicide Rate (Kg/ha) | Antidote Rate (Kg/ha) | Acetochlor + Antidote #1* | | | | Acetochlor + Antidote #22* | | | | Safening Effect Ratio** |
|---|---|---|---|---|---|---|---|---|---|---|
| | | % Corn Injury | | | Safening Effect (% Ave.) | % Corn Injury | | | Safening Effect (% Ave.) | |
| | | PRE (W WO) | PPI (W WO) | | | PRE (W WO) | PPI (W WO) | | | |
| 2.24 | 0.11 | 12  20 (40) | 12  35 (66) | 12  27.5 (56) | | 23  20 (0) | 15  35 (57) | 19  27.5 (31) | | 1.8 |
| 4.48 | 0.22 | 22  45 (51) | 22  65 (66) | 22  55 (60) | | 48  45 (0) | 35  65 (46) | 41.5  55 (25) | | 2.4 |
| 6.72 | 0.34 | 35  68 (49) | 28  72 (61) | 31.5  70 (55) | | 58  68 (15) | 40  72 (44) | 49  70 (30) | | 1.8 |
| 2.24 | 0.15 | 10  20 (50) | 8  35 (77) | 9  27.5 (67) | | 20  20 (0) | 13  35 (63) | 16.5  27.5 (40) | | 1.7 |
| 4.48 | 0.30 | 18  45 (60) | 12  65 (82) | 15  55 (73) | | 37  45 (18) | 28  65 (57) | 32.5  55 (41) | | 1.8 |
| 6.72 | 0.45 | 33  68 (51) | 20  72 (72) | 26.5  70 (62) | | 50  68 (26) | 33  72 (54) | 41.5  70 (41) | | 1.5 |
| 2.24 | 0.22 | 8  20 (60) | 5  35 (86) | 6.5  27.5 (76) | | 17  20 (15) | 12  35 (66) | 14.5  27.5 (47) | | 1.6 |
| 4.48 | 0.45 | 18  45 (60) | 10  65 (85) | 15  55 (73) | | 27  45 (40) | 25  65 (62) | 26  55 (53) | | 1.4 |
| 6.72 | 0.67 | 28  68 (59) | 17  72 (76) | 22.5  70 (68) | | 45  68 (34) | 33  72 (54) | 39  70 (44) | | 1.5 |

*Observations taken at 35 days after treatment
**Safening Effect of Invention Cpd. #1 divided by Safening Effect of Prior Art Cpd. #22; average of all safening effect ratios is 1.7

FIG. 1 shows a comparison of the relative efficacies of the invention antidote compound (Cpd. #1) and the prior art compound (Cpd. #22). Safening effect data for the two antidote compounds are shown at three different antidote use rates (0.11, 0.15, 0.22 Kg/ha) for an acetochlor use rate of 2.24 Kg/ha. Data for this acetochlor use rate are selected for presentation in FIG. 1 because the application rate of 2.24 Kg/ha is the closest rate to actual commercial field use rates, and thus is most significant in demonstrating the practical utility of the invention. FIG. 1 shows results recorded at two different field locations in eastern Missouri. At the first field location, for an acetochlor herbicide application rate of 2.24 kg/ha, the invention antidote was superior to the prior art antidote in safening acetochlor in corn by a factor of about 3-to-1 at the highest antidote use rate, and by a factor of about 6-to-1 at the lowest antidote use rate. At the second field location for an acetochlor herbicide application rate of 2.24 Kg/ha, the invention antidote showed safening efficacy on acetochlor in corn at almost twice the efficacy of the prior art antidote at three different antidote use rates.

FIG. 2 shows a comparison of the relative weed control and corn injury resulting from use of an acetochlor formulation having no antidote, an acetochlor formulation containing prior art antidote compound (Cpd. #22), and an acetochlor formulation containing antidote of the invention (Cpd. #1). The data shown are taken from comparative field tests at two different locations in eastern Missouri (Examples 32 and 33). Corn/weed injury data are shown for the combination of conditions most commercially desirable and thus of most significance in demonstrating the practical utility of the invention. Such combination of commercially-desirable conditions includes the lowest acetochlor use rate (2.24 Kg/ha), with the lowest antidote use rate (0.11 Kg/ha), and involving the simplest field treatment procedure (pre-emergent application of a herbicide + antidote tank-mix formulation). Commercially-acceptable treatments with a herbicide product also required two additional criteria: First, the herbicide product must control the target weeds of concern, particularly the difficult-to-control broadleaf weeds, to a level of at least 85% control; secondly, the injury caused by the herbicide product on corn must be less than 20% injury. FIG. 2 shows that treatment with the acetochlor formulation containing no antidote resulted in too much corn injury at both field locations (28% and 20%) or failed to control the broadleaf weeds, or did both. The acetochlor formulation containing the prior art antidote compound (Cpd. #22) injured corn at both field locations to an excessive degree (23% and 30%). The acetochlor formulation containing the antidote compound of the invention (Cpd. #1) provided both commercially-acceptable broadleaf weed control and commercially-acceptable corn injury at both field locations (12% and 15%).

Although this invention has been described with respect to specific embodiments, the details of these embodiments are not to be construed as limitations.

Various equivalents, changes and modifications may be made without departing from the spirit and scope of this invention, and it is understood that such equivalent embodiments are part of this invention.

What is claimed is:

1. The compound 2-(dichloroacetyl)-1-methyl-1,2,3,4-tetrahydroisoquinoline.

2. A method for reducing herbicide injury to corn due to acetochlor, which comprises applying to the corn locus a herbicidal composition comprising a herbicidally-effective amount of acetochlor and an antidotally-effective amount of the compound 2-(dichloroacetyl)-1-methyl-1,2,3,4-tetrahydroisoquinoline, the herbicide:antidote ratio being within the range of about 2:1 to 50:1.

3. Herbicidal composition comprising a herbicidally-effective amount of acetochlor and an antidotally-effective amount of 2-(dichloroacetyl)-1-methyl-1,2,3,4-tetrahydroisoquinoline, the herbicide:antidote ratio being within the range of about 2:1 to 50:1.

* * * * *

UNITED STATES PATENT AND TRADEMARK OFFICE
CERTIFICATE OF CORRECTION

PATENT NO. : 4,755,218

DATED : July 5, 1988

INVENTOR(S) : Gerhard H. Alt, Harrison R. Hakes, and Ronald J. Brinker

It is certified that error appears in the above-identified patent and that said Letters Patent is hereby corrected as shown below:

Column 2, in the formula, "N-H" should be --N-X--.

Column 14, line 27, the word --of-- was left off before the word "solvent".

Column 39, Table IV, Herbicide No. 5, Antidote No. 8 (at 0.14 kg/ha rate), under Corn W WO - "(55)" should be --(38)--.
                                                        35 57

Column 39, Table IV, Herbicide No. 5, Antidote No. 17 (at 0.56 kg/ha rate), under Corn W WO - "(38)" should be --(55)--.
                                                        20 45

Column 41, Table IV, Herbicide No. 6, Antidote No. 1 (next-last 0.14 kg/ha rate), under Barnyard Grass - "(2)" should be --(0)--.                                   W    WO
                                                       100

Column 43, Table
(second occurre

Signed and Sealed this

Thirtieth Day of April, 1991

*Attest:*

HARRY F. MANBECK, JR.

*Attesting Officer*    Commissioner of Patents and Trademarks